US008828995B2

United States Patent
Boehme et al.

(10) Patent No.: US 8,828,995 B2
(45) Date of Patent: Sep. 9, 2014

(54) BRANCHED OXATHIAZINE DERIVATIVES, METHOD FOR THE PRODUCTION THEREOF, USE THEREOF AS MEDICINE AND DRUG CONTAINING SAID DERIVATIVES AND USE THEREOF

(75) Inventors: Thomas Boehme, Frankfurt am Main (DE); Christian Engel, Frankfurt am Main (DE); Stefan Guessregen, Frankfurt am Main (DE); Torsten Haack, Frankfurt am Main (DE); Kurt Ritter, Frankfurt am Main (DE); Georg Tschank, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 14/003,083

(22) PCT Filed: Mar. 7, 2012

(86) PCT No.: PCT/EP2012/053936
§ 371 (c)(1),
(2), (4) Date: Sep. 4, 2013

(87) PCT Pub. No.: WO2012/120053
PCT Pub. Date: Sep. 13, 2012

(65) Prior Publication Data
US 2013/0345126 A1    Dec. 26, 2013

(30) Foreign Application Priority Data
Mar. 8, 2011    (EP) .................................... 11305241

(51) Int. Cl.
| A61K 31/51 | (2006.01) |
| C07D 291/08 | (2006.01) |
| A61K 45/06 | (2006.01) |
| A61K 31/542 | (2006.01) |
| A61K 31/5415 | (2006.01) |
| C07D 515/04 | (2006.01) |

(52) U.S. Cl.
CPC .............. *C07D 291/08* (2013.01); *A61K 45/06* (2013.01); *A61K 31/542* (2013.01); *A61K 31/5415* (2013.01); *C07D 515/04* (2013.01)
USPC .......................... 514/222.5; 514/222.2; 544/2

(58) Field of Classification Search
None
See application file for complete search history.

(56) References Cited

U.S. PATENT DOCUMENTS

2013/0345128 A1*   12/2013   Boehme et al. ................ 514/6.5

FOREIGN PATENT DOCUMENTS

| WO | WO 02/11722 A1 | 2/2002 |
| WO | WO 2008/073956 A2 | 6/2008 |

OTHER PUBLICATIONS

Suzue, Seigo and Irikura, Tutomu; "Studies on hypoglycemic agents IV. Synthesis of 1, 4, 3, benzoxathizine-4,4-dioxides." Chem. Pharm. Bull. (1963) 16(5) p. 806-813.*
Seigo Suzue et al., Studies on Hypoglycemic Agents. IV. 1) Synthesis of 1,4,3-Benzoxathiazine-4,4-dioxides, Chemical and Pharmaceutical Bulletin, (May 25, 1968), vol. 16, No. 5, pp. 806-813.
Tsuneo Iwakawa et al., Cycloaddition in Synthesis of Sulfonamide Derivatives. IV. One-Pot Synthesis of 3-Dimethylamino-4,1,2-benzoxathiazine 1,1-Dioxides,3-Methoxy-4-methyl-1,2,4-benzothiadizine 1,1-Dioxiade and 3-Dimethylamino-1,4,2-benzodithiazine 1,1-Dioxides, Chemical and Pharmaceutical Bulletin, (Aug. 25, 1991), vol. 39, No. 8, pp. 1939-1943.
International Search Report dated May 11, 2012 issued in PCT/EP2012/053936.

* cited by examiner

Primary Examiner — James H Alstrum Acevedo
Assistant Examiner — Fred Reynolds
(74) Attorney, Agent, or Firm — Scully, Scott, Murphy & Presser, P.C.

(57) ABSTRACT

The invention relates to compounds of formula (I) and to the physiologically compatible salts thereof. Said compounds are suitable, for example, for treating hyperglycemia.

12 Claims, No Drawings

BRANCHED OXATHIAZINE DERIVATIVES, METHOD FOR THE PRODUCTION THEREOF, USE THEREOF AS MEDICINE AND DRUG CONTAINING SAID DERIVATIVES AND USE THEREOF

The invention relates to substituted oxathiazine derivatives and to the physiologically compatible salts thereof.

It was an object of the invention to provide compounds which display a therapeutically utilizable action. More particularly, it was a further object to find novel compounds suitable for treatment of diabetes, hyperglycemia, insulin resistance, obesity, lipid metabolism disorders or other diseases.

The invention therefore relates to the compound of the formula I

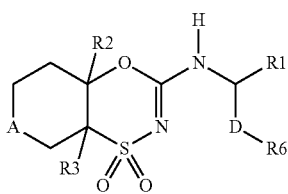

in which
A is $CH_2$, $CF_2$, O;
D is $(C_1-C_6)$-alkylene, $(C_3-C_8)$-cycloalkylene, $(C_1-C_6)$-alkylene-$(C_3-C_8)$-cycloalkylene;
R1 is —$(CH_2)_n$-aryl,
  where the aryl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;
—$(CH_2)_n$-heteroaryl,
  where the heteroaryl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;
n is 0, 1, 2;
R2, R3 are each independently H, $(C_1-C_6)$-alkyl;
R6 is OH, O—(CO)—$NH_2$, $SO_2NH_2$;
and pharmaceutically acceptable salts thereof.

Preference is given to compounds of the formula I in which:
A is $CH_2$;
D is $(C_1-C_6)$-alkylene, $(C_3-C_8)$-cycloalkylene;
R1 is —$(CH_2)_n$-phenyl, —$(CH_2)_n$-pyridinyl,
  where the phenyl radical or pyridinyl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;
n is 0, 1, 2;
R2, R3 are each independently H, $(C_1-C_6)$-alkyl;
R6 is OH, O—(CO)—$NH_2$, $SO_2NH_2$;
and pharmaceutically acceptable salts thereof.

Particular preference is given to compounds of the formula I in which
A is $CH_2$;
D is $(C_1-C_6)$-alkylene;
R1 is phenyl, pyridine
  where the phenyl radical or pyridinyl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;
R2, R3 are each independently H, $(C_1-C_6)$-alkyl;
R6 is OH;
and pharmaceutically acceptable salts thereof.

Very particular preference is given to compounds of the formula I in which
A is $CH_2$;
D is $(C_1-C_2)$-alkylene;
R1 is phenyl,
  where the phenyl radical may be mono- to trisubstituted by F, Cl, Br, I, OH, $CF_3$, $CHF_2$, $CH_2F$, $NO_2$, CN, $OCF_3$, $OCHF_2$, O—$(C_1-C_6)$-alkyl, $(C_1-C_6)$-alkyl, $NH_2$, $NH(C_1-C_6)$-alkyl, $N((C_1-C_6)$-alkyl$)_2$, $SO_2$—$CH_3$, $SO_2$—$NH_2$, $SO_2$—$NH(C_1-C_6)$-alkyl, $SO_2$—$N((C_1-C_6)$-alkyl$)_2$, COOH, COO—$(C_1-C_6)$-alkyl, $CONH_2$, $CONH(C_1-C_6)$-alkyl, $CON((C_1-C_6)$-alkyl$)_2$, $SF_5$;
R2, R3 are each independently H, $(C_1-C_6)$-alkyl;
R6 is OH;
and pharmaceutically acceptable salts thereof.

The invention relates to compounds of the formula I in the form of their tautomers, racemates, racemic mixtures, stereoisomer mixtures, pure stereoisomers, diastereoisomer mixtures and pure diastereoisomers. The mixtures are separated, for example, by a chromatographic route.

Because of their higher water solubility compared to the starting or base compounds, pharmaceutically acceptable salts are particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic acid, phosphoric acid, metaphosphoric acid, nitric acid and sulfuric acid, and of organic acids, for example acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically acceptable basic salts are ammonium salts, alkali metal salts (such as sodium and potassium salts), alkaline earth metal salts (such as magnesium and calcium salts), trometamol (2-amino-2-hydroxymethyl-1,3-propanediol), diethanolamine, lysine or ethylenediamine.

Salts with a pharmaceutically unacceptable anion, for example trifluoroacetate, likewise belong within the framework of the invention as useful intermediates for the preparation or purification of pharmaceutically acceptable salts and/or for use in nontherapeutic, for example in vitro, applications.

The inventive compounds may also be in various polymorphic forms, for example as amorphous and crystalline polymorphic forms. All polymorphic forms of the inventive compounds are within the scope of the invention and are a further aspect of the invention.

All references to "compound(s) of formula I" hereinafter refer to compound(s) of the formula I as described above, and the salts and solvates thereof as described herein.

An alkyl radical is understood to mean a straight-chain or branched hydrocarbyl chain having one to eight carbons, for example methyl, ethyl, isopropyl, tert-butyl, hexyl, heptyl, octyl. The alkyl radicals may be mono- or polysubstituted as described above.

An aryl radical is understood to mean a phenyl, naphthyl, biphenyl, tetrahydronaphthyl, alpha- or beta-tetralonyl, indanyl or indan-1-onyl radical. The aryl radicals may be mono- or polysubstituted by suitable groups as described above.

Heterocycle and heterocyclic radical are understood to mean rings and ring systems which, apart from carbon, also contain heteroatoms, for example nitrogen, oxygen or sulfur. In addition, this definition also includes ring systems in which the heterocycle or the heterocyclic radical is fused to a further ring system. The heterocycle or the heterocyclic radical may be saturated, partly saturated or aromatic.

Suitable "heterocycles" or "heterocyclic radicals" are acridinyl, azepanyl, azocinyl, benzimidazolyl, benzofuryl, benzothienyl, benzothiophenyl, benzoxazolyl, benzothiazolyl, benzotriazolyl, benzotetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]-tetrahydrofuran, 5,6-dihydro-4H-cyclopentathiazol-2-yl, 4,5-dihydrothiazol-2-yl, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, 4,5,6,7-tetrahydrobenzooxazol-2-yl, 4,5,6,7-tetrahydrobenzothiazol-2-yl, 4,5,6,7-tetrahydrobenzoimidazol-2-yl, 4,5,6,7-tetrahydropyrazolo[1,5-a]pyridin-2-yl, tetrahydrofuranyl, tetrahydropyranyl, tetrahydroisoquinolinyl, tetrahydroquinolinyl, 6H-1,2,5-thiadazinyl, thiazolyl, 1,2,3-thiadiazolyl, 1,2,4-thiadiazolyl, 1,2,5-thiadiazolyl, 1,3,4-thiadiazolyl, thienyl, triazinyl, triazolyl, tetrazolyl, thiazolo[4,5-b]pyridinyl, thieno[2,3-d]thiazol-2-yl, tropanyl and xanthenyl.

The heterocycles or heterocyclic radicals may be mono- or polysubstituted by suitable groups as described above.

The compound(s) of the formula I can also be administered in combination with further active ingredients.

The amount of a compound of the formula I required to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram per minute. Suitable infusion solutions for these purposes may contain, for example, 0.1 ng to 10 mg, typically 1 ng to 10 mg, per milliliter. Single doses may contain, for example, 1 mg to 10 g of the active ingredient. Thus, ampoules for injections may contain, for example, from 1 mg to 100 mg, and orally administrable single-dose formulations, for example tablets or capsules, may contain, for example, from 1.0 to 1000 mg, typically from 10 to 600 mg. For treatment of the abovementioned conditions, the compounds of the formula I themselves may be used as the compound, but they are preferably present with a compatible carrier in the form of a pharmaceutical composition. The carrier must of course be acceptable in the sense that it is compatible with the other constituents of the composition and is not harmful to the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Inventive pharmaceutical compositions are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations are also within the scope of the invention. Preference is given to acid- and gastric juice-resistant formulations. Suitable gastric juice-resistant coatings comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units, for example capsules, cachets, lozenges or tablets, each of which contains a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. For example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surfactant(s)/dispersant(s) in a suitable machine. Molded tablets can be produced by molding the pulverulent compound moistened with an inert liquid diluent in a suitable machine.

Pharmaceutical compositions suitable for peroral (sublingual) administration include lozenges which contain a compound of formula I with a flavoring, typically sucrose, and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable inventive compositions generally contain from 0.1 to 5% by weight of the active compound.

Pharmaceutical compositions suitable for rectal administration are preferably in the form of single-dose suppositories. These can be produced by mixing a compound of formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of 0.1 to 15% by weight of the composition, for example 0.5 to 2%.

Transdermal administration is also possible. Pharmaceutical compositions suitable for transdermal uses may be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular option is for the active ingredient to be released by electrotransport or iontophoresis as described, for example, in Pharmaceutical Research, 2(6): 318 (1986).

Further suitable active ingredients for the combination products are:

All antidiabetics mentioned in the Rote Liste 2009, chapter 12; all weight-reducing agents/appetite suppressants mentioned in the Rote Liste 2009, chapter 1; all diuretics mentioned in the Rote Liste 2009, chapter 36; all lipid-lowering agents mentioned in the Rote Liste 2009, chapter 58. They can be combined with the inventive compound of the formula I, especially for a synergistic improvement in action. The active ingredient combination can be administered either by separate administration of the active ingredients to the patient or in the form of combination products in which a plurality of active ingredients are present in one pharmaceutical preparation. When the active ingredients are administered by separate administration of the active ingredients, this can be done simultaneously or successively. Most of the active ingredients mentioned hereinafter are disclosed in the USP Dictionary of USAN and International Drug Names, US Pharmacopeia, Rockville 2006.

Antidiabetics include insulin and insulin derivatives, for example Lantus® (see www.lantus.com) or HMR 1964 or Levemir® (insulin detemir), Humalog® (Insulin Lispro), Humulin®, VIAject™, or those as described in WO2005005477 (Novo Nordisk), fast-acting insulins (see U.S. Pat. No. 6,221,633), inhalable insulins, for example Exubera®, Nasulin™, or oral insulins, for example IN-105 (Nobex) or Oral-lyn™ (Generex Biotechnology), or Technosphere® Insulin (MannKind) or Cobalamin™ oral insulin, or insulins as described in WO2007128815, WO2007128817, or insulins which can be administered transdermally; GLP-1 derivatives and GLP-1 agonists, for example exenatide, liraglutide, or those which have been disclosed in WO 98/08871, WO2005027978, WO2006037811, WO2006037810 by Novo Nordisk A/S, in WO 01/04156 by Zealand or in WO 00/34331 by Beaufour-Ipsen, pramlintide acetate (Symlin; Amylin Pharmaceuticals), AVE-0010, BIM-51077 (R-1583, ITM-077), PC-DAC:Exendin-4 (an exendin-4 analog which is bonded covalently to recombinant human albumin), CVX-73, CVX-98 and CVx-96 (GLP-1 analog which is bonded covalently to a monoclonal antibody which has specific binding sites for the GLP-1 peptide), CNTO-736 (a GLP-1 analog which is bonded to a domain which includes the Fc portion of an antibody), PGC-GLP-1 (GLP-1 bonded to a nanocarrier), agonists, as described, for example, in D. Chen et al., Proc. Natl. Acad. Sci. USA 104 (2007) 943, those as described in WO2006124529, WO2007124461, peptides, for example obinepitide (TM-30338), amylin receptor agonists, as described, for example, in WO2007104789, analogs of the human GLP-1, as described in WO2007120899, and orally active hypoglycemic ingredients.

Antidiabetics also include agonists of the glucose-dependent insulinotropic polypeptide (GIP) receptor, as described, for example, in WO2006121860.

Antidiabetics also include analogs and derivatives of fibroblast growth factor 21 (FGF-21).

The orally active hypoglycemic ingredients preferably include sulfonylureas,
biguanidines,
meglitinides,
oxadiazolidinediones,
thiazolidinediones,
PPAR and RXR modulators,
glucosidase inhibitors,
inhibitors of glycogen phosphorylase,
glucagon receptor antagonists,
glucokinase activators,
inhibitors of fructose 1,6-bisphosphatase,
modulators of glucose transporter 4 (GLUT4),
inhibitors of glutamine:fructose-6-phosphate amidotransferase (GFAT),
GLP-1 agonists,
potassium channel openers, for example pinacidil, cromakalim, diazoxide, or those as described in R. D. Can et al., Diabetes 52, 2003, 2513-2518, in J. B. Hansen et al., Current Medicinal Chemistry 11, 2004, 1595-1615, in T. M. Tagmose et al., J. Med. Chem. 47, 2004, 3202-3211 or in M. J. Coghlan et al., J. Med. Chem. 44, 2001, 1627-1653, or those which have been disclosed in WO 97/26265 and WO 99/03861 by Novo Nordisk A/S,
active ingredients which act on the ATP-dependent potassium channel of the beta cells,
inhibitors of dipeptidyl peptidase-IV (DPP-IV),
insulin sensitizers,
inhibitors of liver enzymes involved in stimulating gluconeogenesis and/or glycogenolysis,
modulators of glucose uptake, of glucose transport and of glucose reabsorption,
modulators of sodium-dependent glucose transporter 1 or 2 (SGLT1, SGLT2),
inhibitors of 11-beta-hydroxysteroid dehydrogenase-1 (11β-HSD1),
inhibitors of protein tyrosine phosphatase-1B (PTP-1B),
nicotinic acid receptor agonists,
inhibitors of hormone-sensitive or endothelial lipases,
inhibitors of acetyl-CoA carboxylase (ACC 1 and/or ACC2) or
inhibitors of GSK-3 beta.

Also included are compounds which modify the lipid metabolism, such as active antihyperlipidemic ingredients and active antilipidemic ingredients,
HMG-CoA reductase inhibitors,
farnesoid X receptor (FXR) antagonists,
fibrates,
cholesterol reabsorption inhibitors, CETP inhibitors,
bile acid absorption inhibitors,
MTP inhibitors,
estrogen receptor gamma agonists (ERR agonists),
sigma-1 receptor antagonists,
antagonists of the somatostatin 5 receptor (SST5 receptor);
compounds which reduce food intake, and
compounds which increase thermogenesis.

In one embodiment of the invention, the compound of the formula I is administered in combination with insulin.

In one embodiment, the compound of the formula I is administered in combination with an active ingredient which acts on the ATP-dependent potassium channel of the beta cells, for example sulfonylureas, for example tolbutamide, glibenclamide, glipizide, gliclazide or glimepiride.

In one embodiment, the compound of the formula I is administered in combination with a tablet which comprises both glimepiride, which is released rapidly, and metformin, which is released over a longer period (as described, for example, in US2007264331).

In one embodiment, the compound of the formula I is administered in combination with a biguanide, for example metformin.

In another embodiment, the compound of the formula I is administered in combination with a meglitinide, for example repaglinide, nateglinide or mitiglinide.

In a further embodiment, the compound of the formula I is administered with a combination of mitiglinide with a glitazone, e.g. pioglitazone hydrochloride.

In a further embodiment, the compound of the formula I is administered with a combination of mitiglinide with an alpha-glucosidase inhibitor.

In a further embodiment, the compound of the formula I is administered in combination with antidiabetic compounds, as described in WO2007095462, WO2007101060, WO2007105650.

In a further embodiment, the compound of the formula I is administered in combination with antihypoglycemic compounds, as described in WO2007137008.

In one embodiment, the compound of the formula I is administered in combination with a thiazolidinedione, for example troglitazone, ciglitazone, pioglitazone, rosiglitazone or the compounds disclosed in WO 97/41097 to Dr. Reddy's Research Foundation, especially 5-[[4-[(3,4-dihydro-3-methyl-4-oxo-2-quinazolinylmethoxy]phenyl]methyl]-2,4-thiazolidinedione.

In one embodiment of the invention, the compound of the formula I is administered in combination with a PPAR gamma agonist, for example rosiglitazone, pioglitazone, JTT-501, G1 262570, R-483, CS-011 (rivoglitazone), DRL-17564, DRF-2593 (balaglitazone), or those as described in WO2007060992, WO2007100027, WO2007103252, WO2007122970.

In one embodiment of the invention, the compound of the formula I is administered in combination with Competact™, a solid combination of pioglitazone hydrochloride with metformin hydrochloride.

In one embodiment of the invention, the compound of the formula I is administered in combination with Tandemact™, a solid combination of pioglitazone with glimepiride.

In a further embodiment of the invention, the compound of the formula I is administered in combination with a solid combination of pioglitazone hydrochloride with an angiotensin II agonist, for example TAK-536.

In one embodiment of the invention, the compound of the formula I is administered in combination with a PPAR alpha agonist or mixed PPAR alpha/PPAR delta agonist, for example GW9578, GW-590735, K-111, LY-674, KRP-101, DRF-10945, LY-518674, CP-900691, BMS-687453, BMS-711939, or those as described in WO2001040207, WO2002096894, WO2005097076, WO2007056771, WO2007087448, WO2007089667, WO2007089557, WO2007102515, WO2007103252, JP2007246474, WO2007118963, WO2007118964, WO2007126043.

In one embodiment of the invention, the compound of the formula I is administered in combination with a mixed PPAR alpha/gamma agonist, for example naveglitazar, LY-510929, ONO-5129, E-3030, AVE 8042, AVE 8134, AVE 0847, CKD-501 (lobeglitazone sulfate), MBX-213, or as described in WO 00/64888, WO 00/64876, WO03/020269, WO2007099553, US2007276041, WO2007085135, WO2007085136, or in J. P. Berger et al., TRENDS in Pharmacological Sciences 28(5), 244-251, 2005.

In one embodiment of the invention, the compound of the formula I is administered in combination with a PPAR delta agonist, for example GW-501516, or as described in WO2006059744, WO2006084176, WO2006029699, WO2007039172, WO2007039178, WO2007071766, WO2007101864, US2007244094, WO2007119887.

In one embodiment of the invention, the compound of the formula I is administered in combination with a pan-SP-PARM (selective PPAR modulator alpha, gamma, delta), for example GFT-505.

In one embodiment, the compound of the formula I is administered in combination with metaglidasen or with MBX-2044 or other partial PPAR gamma agonists/antagonists.

In one embodiment, the compound of the formula I is administered in combination with an α-glucosidase inhibitor, for example miglitol or acarbose, or those as described, for example, in WO2007114532, WO2007140230.

In one embodiment, the compound of the formula I is administered in combination with an inhibitor of glycogen phosphorylase, for example PSN-357 or FR-258900, or those as described in WO2003084922, WO2004007455, WO2005073229-31, WO2005067932.

In one embodiment, the compound of the formula I is administered in combination with glucagon receptor antagonists, for example A-770077 or NNC-25-2504 or as described in WO2004100875, WO2005065680, WO2006086488, WO2007106181, WO2007111864, WO2007120270, WO2007120284, WO2007123581, WO2007136577.

In a further embodiment, the compound of the formula I is administered in combination with an antisense compound, e.g. ISIS-325568, which inhibits the production of the glucagon receptor.

In one embodiment, the compound of the formula I is administered in combination with activators of glucokinase, for example LY-2121260 (WO2004063179), PSN-105, PSN-110, GKA-50, or those as described, for example, in WO2004072031, WO2004072066, WO2005080360, WO2005044801, WO2006016194, WO2006058923, WO2006112549, WO2006125972, WO2007017549, WO2007017649, WO2007007910, WO2007007040-42, WO2007006760-61, WO2007006814, WO2007007886, WO2007028135, WO2007031739, WO2007041365, WO2007041366, WO2007037534, WO2007043638, WO2007053345, WO2007051846, WO2007051845, WO2007053765, WO2007051847, WO2007061923, WO2007075847, WO2007089512, WO2007104034, WO2007117381, WO2007122482, WO2007125103, WO2007125105, US2007281942.

In one embodiment, the compound of the formula I is administered in combination with an inhibitor of gluconeogenesis, for example FR-225654.

In one embodiment, the compound of the formula I is administered in combination with inhibitors of fructose 1,6-bisphosphatase (FBPase), for example CS-917 (MB-06322) or MB-07803, or those as described in WO2006023515, WO2006104030, WO2007014619, WO2007137962.

In one embodiment, the compound of the formula I is administered in combination with modulators of glucose transporter 4 (GLUT4), for example KST-48 (D.-O. Lee et al.: Arzneim.-Forsch. Drug Res. 54 (12), 835 (2004)).

In one embodiment, the compound of the formula I is administered in combination with inhibitors of glutamine: fructose-6-phosphate amidotransferase (GFAT), as described, for example, in WO2004101528.

In one embodiment, the compound of the formula I is administered in combination with inhibitors of dipeptidyl peptidase IV (DPP-IV), for example vildagliptin (LAF-237), sitagliptin (MK-0431), sitagliptin phosphate, saxagliptin ((BMS-477118), GSK-823093, PSN-9301, SYR-322, SYR-619, TA-6666, TS-021, GRC-8200, GW-825964X, KRP-104, DP-893, ABT-341, ABT-279 or another salt thereof, S-40010, S-40755, PF-00734200, BI-1356, PHX-1149, alogliptin, or those compounds as described in WO2003074500, WO2003106456, WO2004037169, WO200450658, WO2005037828, WO2005058901, WO2005012312, WO2005/012308, WO2006039325, WO2006058064, WO2006015691, WO2006015701, WO2006015699, WO2006015700, WO2006018117, WO2006099943, WO2006099941, JP2006160733, WO2006071752, WO2006065826, WO2006078676, WO2006073167, WO2006068163, WO2006085685, WO2006090915, WO2006104356, WO2006127530, WO2006111261, WO2007015767 (LY-2463665), WO2007024993, WO2007029086, WO2007063928, WO2007070434, WO2007071738, WO2007077508, WO2007087231, WO2007097931, WO2007099385, WO2007100374, WO2007112347, WO2007112669, WO2007113226, WO2007113634, WO2007115821, WO2007116092, US2007259900, EP1852108, US2007270492, WO2007126745, WO2007136603.

In one embodiment, the compound of the formula I is administered in combination with Janumet™, a solid combination of sitagliptin phosphate with metformin hydrochloride.

In one embodiment, the compound of the formula I is administered in combination with Eucreas®, a solid combination of vildagliptin with metformin hydrochloride.

In one embodiment, the compound of the formula I is administered in combination with a combination of a DPP-IV inhibitor with omega-3 fatty acids or omega-3 fatty acid esters, as described, for example, in WO2007128801.

In one embodiment, the compound of the formula I is administered in combination with a substance which enhances insulin secretion, for example KCP-265 (WO2003097064), or those as described in WO2007026761.

In one embodiment, the compound of the formula I is administered in combination with agonists of the glucose-dependent insulinotropic receptor (GDR), for example APD-668.

In one embodiment of the invention, the compound of the formula I is administered in combination with an ATP citrate lyase inhibitor, for example SB-204990.

In one embodiment, the compound of the formula I is administered in combination with modulators of the sodium-dependent glucose transporter 1 or 2 (SGLT1, SGLT2), for example KGA-2727, T-1095, SGL-0010, AVE 2268, SAR 7226, SGL-5083, SGL-5085, SGL-5094, ISIS-388626, sergliflozin or dapagliflozin, or as described, for example, in WO2004007517, WO200452903, WO200452902, PCT/EP2005/005959, WO2005085237, JP2004359630, WO2005121161, WO2006018150, WO2006035796, WO2006062224, WO2006058597, WO2006073197, WO2006080577, WO2006087997, WO2006108842, WO2007000445, WO2007014895, WO2007080170, WO2007093610, WO2007126117, WO2007128480, WO2007129668, US2007275907, WO2007136116, or by A. L. Handlon in Expert Opin. Ther. Patents (2005) 15(11), 1531-1540.

In one embodiment, the compound of the formula I is administered in combination with inhibitors of 11-beta-hydroxysteroid dehydrogenase 1 (11β-HSD1), for example BVT-2733, JNJ-25918646, INCB-13739, DIO-92 ((−)-ketoconazole) or those as described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005063247, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109, WO2006074244, WO2006078006, WO2006106423, WO2006132436, WO2006134481, WO2006134467, WO2006135795, WO2006136502, WO2006138508, WO2006138695, WO2006133926, WO2007003521, WO2007007688, US2007066584, WO2007029021, WO2007047625, WO2007051811, WO2007051810, WO2007057768, WO2007058346, WO2007061661, WO2007068330, WO2007070506, WO2007087150, WO2007092435, WO2007089683, WO2007101270, WO2007105753, WO2007107470, WO2007107550, WO2007111921, US2007207985, US2007208001, WO2007115935, WO2007118185, WO2007122411, WO2007124329, WO2007124337, WO2007124254, WO2007127688, WO2007127693, WO2007127704, WO2007127726, WO2007127763, WO2007127765, WO2007127901, US2007270424, JP2007291075, WO2007130898, WO2007135427.

In one embodiment, the compound of the formula I is administered in combination with inhibitors of protein tyrosine phosphatase 1B (PTP-1B), as described, for example, in WO200119830-31, WO200117516, WO2004506446, WO2005012295, WO2005116003, WO2005116003, WO2006007959, DE 10 2004 060542.4, WO2007009911, WO2007028145, WO2007067612-615, WO2007081755, WO2007115058.

In one embodiment of the invention, the compound of the formula I is administered in combination with an agonist of GPR109A (HM74A receptor agonists; NAR agonists (nicotinic acid receptor agonists)), for example nicotinic acid or "extended release niacin" in conjunction with MK-0524A (laropiprant) or MK-0524, or those compounds as described in WO2006045565, WO2006045564, WO2006069242, WO2006085108, WO2006085112, WO2006085113, WO2006124490, WO2006113150, WO2007017261, WO2007017262, WO2007017265, WO2007015744, WO2007027532, WO2007092364, WO2007120575, WO2007134986.

In another embodiment of the invention, the compound of the formula I is administered in combination with a solid combination of niacin with simvastatin.

In another embodiment of the invention, the compound of the formula I is administered in combination with nicotinic acid or extended release niacin in conjunction with MK-0524A (laropiprant).

In a further embodiment of the invention, the compound of the formula I is administered in combination with nicotinic acid or extended release niacin in conjunction with MK-0524A (laropiprant) and with simvastatin.

In another embodiment of the invention, the compound of the formula I is administered in combination with an agonist of GPR116, as described, for example, in WO2006067531, WO2006067532.

In one embodiment, the compound of the formula I is administered in combination with modulators of GPR40, as described, for example, in WO2007013689, WO2007033002, WO2007106469, US2007265332, WO2007123225, WO2007131619, WO2007131620, WO2007131621, US2007265332, WO2007131622, WO2007136572.

In one embodiment, the compound of the formula I is administered in combination with GPR119b modulators, as described, for example, in WO2004041274.

In one embodiment, the compound of the formula I is administered in combination with modulators of GPR119 (G protein-coupled glucose-dependent insulinotropic receptor), for example PSN-119-1, or those as described, for example, in WO2005090336, WO2006071609, WO2006135826, WO2007105766, WO2008120661, WO2009040288, WO2009058944, WO2009108525, WO2009111214.

In a further embodiment, the compound of the formula I is administered in combination with modulators of GPR120, as described, for example, in EP1688138.

In one embodiment, the compound of the formula I is administered in combination with inhibitors of hormone-sensitive lipase (HSL) and/or phospholipases, as described, for example, in WO2005073199, WO2006074957, WO2006087309, WO2006111321, WO2007042178, WO2007119837.

In one embodiment, the compound of the formula I is administered in combination with inhibitors of endothelial lipase, as described, for example, in WO2007110216.

In one embodiment, the compound of the formula I is administered in combination with a phospholipase A2 inhibitor, for example darapladib or A-002.

In one embodiment, the compound of the formula I is administered in combination with myricitrin, a lipase inhibitor (WO2007119827).

In one embodiment, the compound of the formula I is administered in combination with an inhibitor of glycogen synthase kinase-3 beta (GSK-3 beta), as described, for example, in US2005222220, WO2005085230, WO2005111018, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117, WO2007073117, WO2007083978, WO2007120102, WO2007122634, WO2007125109, WO2007125110.

In one embodiment, the compound of the formula I is administered in combination with an inhibitor of phosphoenolpyruvate carboxykinase (PEPCK), for example those as described in WO2004074288.

In one embodiment, the compound of the formula I is administered in combination with an inhibitor of serum/glucocorticoid-regulated kinase (SGK), as described, for example, in WO2006072354, WO2007093264.

In one embodiment, the compound of the formula I is administered in combination with an inhibitor of protein kinase C beta (PKC beta), for example ruboxistaurin.

In a further embodiment, the compound of the formula I is administered in combination with an activator of the AMP-activated protein kinase (AMPK), as described, for example, in WO2007062568.

In one embodiment, the compound of the formula I is administered in combination with an inhibitor of ceramide kinase, as described, for example, in WO2007112914.

In a further embodiment, the compound of the formula I is administered in combination with an inhibitor of MAPK-interacting kinase 2 (MNK2), as described, for example, in WO2007104053, WO2007115822.

In one embodiment, the compound of the formula I is administered in combination with inhibitors of "I-kappaB kinase" (IKK inhibitors), as described, for example, in WO2001000610, WO2001030774, WO2004022057, WO2004022553, WO2005097129, WO2005113544, US2007244140.

In one embodiment of the invention, the compound of the formula I is administered in combination with an HMG-CoA reductase inhibitor such as simvastatin, fluvastatin, pravastatin, lovastatin, atorvastatin, cerivastatin, rosuvastatin, L-659699, or those as described in US2007249583.

In a further embodiment of the invention, the compound of the formula I is administered in combination with a farnesoid X receptor (FXR) antagonist, as described, for example, in WO2007052843, WO2007070796, WO2007092751, JP2007230909, WO2007095174, WO2007140174, WO2007140183.

In another embodiment of the invention, the compound of the formula I is administered in combination with a ligand of the liver X receptor (LXR), as described, for example, in WO2007092965.

In one embodiment of the invention, the compound of the formula I is administered in combination with a fibrate, for example fenofibrate, clofibrate, bezafibrate.

In one embodiment of the invention, the compound of the formula I is administered in combination with fibrates, for example the choline salt of fenofibrate (SLV-348).

In one embodiment of the invention, the compound of the formula I is administered in combination with fibrates, for example the choline salt of fenofibrate and an HMG-CoA reductase inhibitor, for example rosuvastatin.

In a further embodiment of the invention, the compound of the formula I is administered in combination with bezafibrate and diflunisal.

In a further embodiment of the invention, the compound of the formula I is administered in combination with a solid combination of fenofibrate or a salt thereof with simvastatin, rosuvastatin, fluvastatin, lovastatin, cerivastatin, pravastatin or atorvastatin.

In a further embodiment of the invention, the compound of the formula I is administered in combination with Synordia (R), a solid combination of fenofibrate with metformin.

In one embodiment of the invention, the compound of the formula I is administered in combination with a cholesterol absorption inhibitor, for example ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464, WO2005000353 (Kotobuki Pharmaceutical Co. Ltd.) or WO2005044256 or WO2005062824 (Merck & Co.) or WO2005061451 and WO2005061452 (AstraZeneca AB) and WO2006017257 (Phenomix) or WO2005033100 (Lipideon Biotechnology AG), or as described in WO2002050060, WO2002050068, WO2004000803, WO2004000804, WO2004000805, WO2004087655, WO2004097655, WO2005047248, WO2006086562, WO2006102674, WO2006116499, WO2006121861, WO2006122186, WO2006122216, WO2006127893, WO2006137794, WO2006137796, WO2006137782, WO2006137793, WO2006137797, WO2006137795, WO2006137792, WO2006138163, WO2007059871, US2007232688, WO2007126358.

In one embodiment of the invention, the compound of the formula I is administered in combination with Vytorin™, a solid combination of ezetimibe with simvastatin.

In one embodiment of the invention, the compound of the formula I is administered in combination with a solid combination of ezetimibe with atorvastatin.

In one embodiment of the invention, the compound of the formula I is administered in combination with a solid combination of ezetimibe with fenofibrate.

In one embodiment of the invention, the further active ingredient is a diphenylazetidinone derivative, as described, for example, in U.S. Pat. No. 6,992,067 or U.S. Pat. No. 7,205,290.

In a further embodiment of the invention, the further active ingredient is a diphenylazetidinone derivative, as described, for example, in U.S. Pat. No. 6,992,067 or U.S. Pat. No. 7,205,290, combined with a statin, for example simvastatin, fluvastatin, pravastatin, lovastatin, cerivastatin, atorvastatin or rosuvastatin.

In one embodiment of the invention, the compound of the formula I is administered in combination with a solid combination of lapaquistat, a squalene synthase inhibitor, with atorvastatin.

In one embodiment of the invention, the compound of the formula I is administered in combination with a CETP inhibitor, for example torcetrapib, anacetrapib or JTT-705, or those as described in WO2006002342, WO2006010422, WO2006012093, WO2006073973, WO2006072362, WO2007088996, WO2007088999, US2007185058, US2007185113, US2007185154, US2007185182, WO2006097169, WO2007041494, WO2007090752, WO2007107243, WO2007120621, US2007265252, US2007265304, WO2007128568, WO2007132906.

In one embodiment of the invention, the compound of the formula I is administered in combination with bile acid reabsorption inhibitor (see, for example, U.S. Pat. No. 6,245,744, U.S. Pat. No. 6,221,897 or WO00/61568), for example HMR 1741, or those as described in DE 10 2005 033099.1 and DE 10 2005 033100.9, WO2007009655-56.

In one embodiment, the compound of the formula I is administered in combination with agonists of GPBAR1 (G-protein-coupled bile acid receptor-1; TGR5), as described, for example, in WO2007110237, WO2007127505.

In one embodiment of the invention, the compound of the formula I is administered in combination with a polymeric bile acid adsorber, for example cholestyramine, colesevelam hydrochloride.

In one embodiment of the invention, the compound of the formula I is administered in combination with a chewing gum comprising phytosterols (Reductol™)

In one embodiment of the invention, the compound of the formula I is administered in combination with an inhibitor of the microsomal triglyceride transfer protein (MTP inhibitor), for example implitapide, BMS-201038, R-103757, AS-1552133, SLx-4090, AEGR-733, or those as described in WO2005085226, WO2005121091, WO2006010423, WO2006113910.

In another embodiment of the invention, the compound of the formula I is administered in combination with an antagonist of the somatostatin 5 receptor (SST5 receptor), for example those as described in WO2006094682.

In one embodiment of the invention, the compound of the formula I is administered in combination with an ACAT inhibitor, for example avasimibe, SMP-797 or KY-382.

In a further embodiment of the invention, the compound of the formula I is administered in combination with an inhibitor of liver carnitine palmitoyltransferase 1 (L-CPT1), as described, for example, in WO2007063012, WO2007096251 (ST-3473).

In one embodiment of the invention, the compound of the formula I is administered in combination with a squalene synthetase inhibitor, for example BMS-188494, TAK-475 (lapaquistat acetate), or as described in WO2005077907, JP2007022943.

In one embodiment of the invention, the compound of the formula I is administered in combination with ISIS-301012 (mipomersen), an antisense oligonucleotide which is capable of regulating the apolipoprotein B gene.

In one embodiment of the invention, the compound of the formula I is administered in combination with an LDL receptor inducer (see U.S. Pat. No. 6,342,512), for example HMR1171, HMR1586, or those as described in WO2005097738.

In one embodiment of the invention, the compound of the formula I is administered in combination with an ABCA1 expression enhancer, as described, for example, in WO2006072393.

In one embodiment of the invention, the compound of the formula I is administered in combination with a lipoprotein lipase modulator, for example ibrolipim (NO-1886).

In one embodiment of the invention, the compound of the formula I is administered in combination with a lipoprotein (a) antagonist, for example gemcabene (CI-1027).

In one embodiment of the invention, the compound of the formula I is administered in combination with a lipase inhibitor, for example orlistat or cetilistat (ATL-962).

In one embodiment of the invention, the compound of the formula I is administered in combination with an adenosine A2B receptor agonist (adenosine A2B R), for example ATL-801.

In another embodiment of the invention, the compound of the formula I is administered in combination with a modulator of adenosine A2A and/or adenosine A3 receptors, as described, for example, in WO2007111954, WO2007121918, WO2007121921, WO2007121923.

In one embodiment of the invention, the compound of the formula I is administered in combination with an adenosine A2B receptor antagonist (adenosine A2B R), as described in US2007270433.

In one embodiment, the compound of the formula I is administered in combination with inhibitors of acetyl-CoA carboxylase (ACC™ and/or ACC2), for example those as described in WO199946262, WO200372197, WO2003072197, WO2005044814, WO2005108370, JP2006131559, WO2007011809, WO2007011811, WO2007013691, WO2007095601-603, WO2007119833.

In another embodiment, the compound of the formula I is administered in combination with modulators of microsomal acyl-CoA:glycerol-3-phosphate acyltransferase 3 (GPAT3, described in WO2007100789) or with modulators of microsomal acyl-CoA:glycerol-3-phosphate acyltransferase 4 (GPAT4, described in WO2007100833).

In a further embodiment, the compound of the formula I is administered in combination with modulators of xanthine oxidoreductase (XOR).

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists, for example 4-[(4-aminoquinazolin-2-ylamino)methyl]-cyclohexylmethylnaphthalene-1-sulfonamide hydrochloride (CGP 71683A);

NPY-5 receptor antagonists, such as L-152804 or the compound "NPY-5-BY" from Banyu, or as described, for example, in WO2006001318, WO2007103295, WO2007125952;

NPY-4 receptor antagonists, as described, for example, in WO200703 8942;

NPY-2 receptor antagonists, as described, for example, in WO2007038943;

peptide YY 3-36 (PYY3-36) or analogous compounds, for example CJC-1682 (PYY3-36 conjugated with human serum albumin via Cys34) or CJC-1643 (derivative of PYY3-36, which is conjugated in vivo to serum albumin), or those as described in WO2005080424, WO2006095166;

derivatives of the peptide obestatin, as described by WO2006096847;

CB1R (cannabinoid receptor 1) antagonists, (for example rimonabant, surinabant (SR147778), SLV-319, AVE-1625, taranabant (MK-0364) or salts thereof, V-24343 or those compounds as described in, for example, EP 0656354, WO 00/15609, WO2001/64632-64634, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006047516, WO2006060461, WO2006067428, WO2006067443, WO2006087480, WO2006087476, WO2006100208, WO2006106054, WO2006111849, WO2006113704, WO2007009705, WO2007017124, WO2007017126, WO2007018459, WO2007018460, WO2007016460, WO2007020502, WO2007026215, WO2007028849, WO2007031720, WO2007031721, WO2007036945, WO2007038045, WO2007039740, US20070015810, WO2007046548, WO2007047737, WO2007057687, WO2007062193, WO2007064272, WO2007079681, WO2007084319, WO2007084450, WO2007086080, EP1816125, US2007213302, WO2007095513, WO2007096764, US2007254863, WO2007119001, WO2007120454, WO2007121687, WO2007123949, US2007259934, WO2007131219, WO2007133820, WO2007136607, WO2007136571, US7297710, WO2007138050, WO2007140385, WO2007140439);

cannabinoid receptor 1/cannabinoid receptor 2 (CB 1/CB2) modulating compounds, for example delta-9-tetrahydrocannabivarin, or those as described, for example, in WO2007001939, WO2007044215, WO2007047737, WO2007095513, WO2007096764, WO2007112399, WO2007112402;

modulators of FAAH (fatty acid amide hydrolase), as described, for example, in WO2007140005;

vanilloid 1 receptor modulators (modulators of TRPV1), as described, for example, in WO2007091948, WO2007129188, WO2007133637;

activators of the capsaicin receptor, as described, for example, in JP2007210969;

agonists of the prostaglandin receptor, for example bimatoprost or those compounds as described in WO2007111806;

MC4 receptor agonists (melanocortin-4 receptor agonists, MC4R agonists, for example N-[2-(3a-benzyl-2-methyl-3-oxo-2,3,3a,4,6,7-hexahydropyrazolo[4,3-c]-pyridin-5-yl)-1-(4-chlorophenyl)-2-oxoethyl]-1-amino-1,2,3,4-tetrahydronaphthalene-2-carboxamide; (WO 01/91752)) or LB53280, LB53279, LB53278 or THIQ, MB243, RY764, CHIR-785, PT-141, MK-0493, or those as described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2005042516, WO2005040109, WO2005030797, US20040224901, WO200501921, WO200509184, WO2005000339, EP1460069, WO2005047253, WO2005047251, WO2005118573, EP1538159, WO2004072076, WO2004072077, WO2006021655-57, WO2007009894, WO2007015162, WO2007041061, WO2007041052, JP2007131570, EP-1842846, WO2007096186, WO2007096763;

orexin receptor 1 antagonists (OX1R antagonists), orexin receptor 2 antagonists (OX2R antagonists) or mixed OX1R/OX2R antagonists (e.g. 1-(2-methylbenzoxazol-6-yl)-3-[1,5]naphthyridin-4-ylurea hydrochloride (SB-334867-A), or those as described, for example, in WO200196302, WO200185693, WO2004085403, WO2005075458, WO2006067224, WO2007085718, WO2007088276, WO2007116374; WO2007122591, WO2007126934, WO2007126935);

histamine H3 receptor antagonists/inverse agonists (e.g. 3-cyclohexyl-1-(4,4-dimethyl-1,4,6,7-tetrahydroimidazo[4, 5-c]pyridin-5-yl)propan-1-one oxalic acid salt (WO 00/63208), or those as described in WO200064884, WO2005082893, US2005171181 (e.g. PF-00389027), WO2006107661, WO2007003804, WO2007016496, WO2007020213, WO2007049798, WO2007055418, WO2007057329, WO2007065820, WO2007068620, WO2007068641, WO2007075629, WO2007080140, WO2007082840, WO2007088450, WO2007088462, WO2007094962, WO2007099423, WO2007100990, WO2007105053, WO2007106349, WO2007110364, WO2007115938, WO2007131907, WO2007133561, US2007270440, WO2007135111);

histamine H1/histamine H3 modulators, for example betahistine or its dihydrochloride;

CRF antagonists (e.g. [2-methyl-9-(2,4,6-trimethylphenyl)-9H-1,3,9-triazafluoren-4-yl]dipropylamine (WO 00/66585) or those CRF1 antagonists as described in WO2007105113, WO2007133756);

CRF BP antagonists (e.g. urocortin);

urocortin agonists;

agonists of the beta-3 adrenoceptor, for example 1-(4-chloro-3-methanesulfonylmethylphenyl)-2-[2-(2,3-dimethyl-1H-indol-6-yloxy)ethylamino]ethanol hydrochloride (WO 01/83451) or solabegron (GW-427353) or N-5984 (KRP-204), or those as described in JP2006111553, WO2002038543, WO2002038544, WO2007048840-843;

MSH (melanocyte-stimulating hormone) agonists;

MCH (melanine-concentrating hormone) receptor antagonists (for example NBI-845, A-761, A-665798, A-798, ATC-0175, T-226296, T-71, GW-803430, or those compounds as described in WO2005085200, WO2005019240, WO2004011438, WO2004012648, WO2003015769, WO2004072025, WO2005070898, WO2005070925, WO2004039780, WO2004092181, WO2003033476, WO2002006245, WO2002089729, WO2002002744, WO2003004027, FR2868780, WO2006010446, WO2006038680, WO2006044293, WO2006044174, JP2006176443, WO2006018280, WO2006018279, WO2006118320, WO2006130075, WO2007018248, WO2007012661, WO2007029847, WO2007024004, WO2007039462, WO2007042660, WO2007042668, WO2007042669, US2007093508, US2007093509, WO2007048802, JP2007091649, WO2007092416; WO2007093363-366, WO2007114902, WO2007114916);

CCK-A (CCK-1) agonists (for example {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525) or SR-146131 (WO 0244150) or SSR-125180), or those as described in WO2005116034, WO2007120655, WO2007120688, WO2007120718;

serotonin reuptake inhibitors (for example dexfenfluramine);

mixed serotonin/dopamine reuptake inhibitors (e.g. bupropion), or solid combinations of bupropion with naltrexone or bupropion with zonisamide;

mixed reuptake inhibitors, for example DOV-21947;

mixed serotoninergic and noradrenergic compounds (e.g. WO 00/71549);

5-HT receptor agonists, for example 1-(3-ethylbenzofuran-7-yl)piperazine oxalic acid salt (WO 01/09111);

mixed dopamine/norepinephrine/acetylcholine reuptake inhibitors (e.g. tesofensine), or those as described, for example, in WO2006085118;

5-HT2C receptor agonists (for example lorcaserine hydrochloride (APD-356) or BVT-933, or those as described in WO200077010, WO200077001-02, WO2005019180, WO2003064423, WO200242304, WO2005035533, WO2005082859, WO2006004937, US2006025601, WO2006028961, WO2006077025, WO2006103511, WO2007028132, WO2007084622, US2007249709; WO2007132841, WO2007140213);

5-HT6 receptor modulators, for example E-6837, BVT-74316 or PRX-07034, or those as described, for example, in WO2005058858, WO2007054257, WO2007107373, agonists of estrogen receptor gamma (ERR agonists), as described, for example, in WO2007131005;

sigma-1 receptor antagonists, as described, for example, in WO2007098953, WO2007098961;

muscarin 3 receptor (M3R) antagonists, as described, for example, in WO2007110782;

bombesin receptor agonists (BRS-3 agonists);

galanin receptor antagonists;

growth hormone (e.g. human growth hormone or AOD-9604);

growth hormone releasing compounds (tert-butyl 6-benzyloxy-1-(2-diisopropylaminoethylcarbamoyl)-3,4-dihydro-1H-isoquinoline-2-carboxylate (WO 01/85695));

growth hormone secretagogue receptor antagonists (ghrelin antagonists), for example A-778193, or those as described in WO2005030734, WO2007127457;

growth hormone secretagogue receptor modulators, for example JMV-2959, JMV-3002, JMV-2810, JMV-2951, or those as described in WO2006012577 (e.g. YIL-781 or YIL-870), WO2007079239;

TRH agonists (see, for example, EP 0 462 884);

decoupling protein 2 or 3 modulators;

leptin agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);

dopamine agonists (DA agonists, for example bromocriptine, Doprexin);

lipase/amylase inhibitors (e.g. WO 00/40569);

inhibitors of diacylglycerol O-acyltransferases (DGATs), for example BAY-74-4113, or as described, for example, in US2004/0224997, WO2004094618, WO200058491, WO2005044250, WO2005072740, JP2005206492, WO2005013907, WO2006004200, WO2006019020, WO2006064189, WO2006082952, WO2006120125, WO2006113919, WO2006134317, WO2007016538, WO2007060140, JP2007131584, WO2007071966, WO2007126957, WO2007137103, WO2007137107, WO2007138304, WO2007138311;

inhibitors of fatty acid synthase (FAS), for example C75, or those as described in WO2004005277;

inhibitors of stearoyl-CoA delta9 desaturase (SCD1), as described, for example in WO2007009236, WO2007044085, WO2007046867, WO2007046868, WO20070501124, WO2007056846, WO2007071023, WO2007130075, WO2007134457, WO2007136746;

inhibitors of "adipocyte fatty acid-binding protein aP2", for example BMS-309403;

activators of adiponectin secretion, as described, for example, in WO2006082978;

promoters of adiponectin production, as described, for example, in WO2007125946;

oxyntomodulin;

oleoyl-estrone or agonists or partial agonists of the thyroid hormone receptor (thyroid hormone receptor agonists), for example: KB-2115 or DITPA, or those as described in WO20058279, WO200172692, WO200194293, WO2003084915, WO2004018421, WO2005092316, WO2007003419, WO2007009913, WO2007039125, WO2007110225, WO2007110226,

WO2007128492, WO2007132475, WO2007134864;

or agonists of the thyroid hormone receptor beta (TR-beta), for example MB-07811 or MB-07344.

In one embodiment of the invention, the compound of the formula I is administered in combination with an inhibitor of site-1 protease (S1P), for example PF-429242.

In a further embodiment of the invention, the compound of the formula I is administered in combination with an RNAi therapeutic agent directed against PCSK9 (proprotein convertase subtilisinfkexin type 9).

In one embodiment, the compound of the formula I is administered in combination with Omacor® or Lovaza™ (omega-3 fatty acid ester; highly concentrated ethyl ester of eicosapentaenoic acid and of docosahexaenoic acid).

In one embodiment, the compound of the formula I is administered in combination with lycopene.

In one embodiment of the invention, the compound of the formula I is administered in combination with an antioxidant, for example OPC-14117, succinobucol, probucol, tocopherol, ascorbic acid, β-carotene or selenium.

In one embodiment of the invention, the compound of the formula I is administered in combination with a vitamin, for example vitamin B6 or vitamin B 12.

In one embodiment, the compound of the formula I is administered in combination with more than one of the aforementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

In another embodiment, the compound of the formula I is administered in combination with an inhibitor of carboanhydrase type 2 (carbonic anhydrase type 2), for example those as described in WO2007065948.

In another embodiment, the compound of the formula I is administered in combination with topiramat.

In a further embodiment, the compound of the formula I is administered in combination with a solid combination of topiramat with phentermine (Qnexa™)

In a further embodiment, the compound of the formula I is administered in combination with an antisense compound, e.g. ISIS-377131, which inhibits the production of the glucocorticoid receptor.

In one embodiment, the compound of the formula I is administered in combination with an agonist of the RUP3 receptor, as described, for example, in WO2007035355.

In another embodiment, the compound of the formula I is administered in combination with an activator of the gene which codes for ataxia telangiectasia mutated (ATM) protein kinase, for example chloroquine.

In one embodiment, the compound of the formula I is administered in combination with a tau protein kinase 1 inhibitor (TPK1 inhibitor), as described, for example, in WO2007119463.

In one embodiment, the compound of the formula I is administered in combination with a "c-Jun N-terminal kinase" inhibitor (JNK inhibitor), as described, for example, in WO2007125405.

In one embodiment, the compound of the formula I is administered in combination with an endothelin A receptor antagonist, for example avosentan (SPP-301).

In one embodiment, the compound of the formula I is administered in combination with modulators of the glucocorticoid receptor (GR), for example KB-3305 or those compounds as described, for example, in WO2005090336, WO2006071609, WO2006135826, WO2007105766.

In one embodiment, the further active ingredient is vareniclin tartrate, a partial agonist of the alpha 4-beta 2 nicotinic acetylcholine receptor.

In one embodiment, the further active ingredient is trodusquemine.

In one embodiment, the further active ingredient is a modulator of the enzyme SIRT1 (an NAD+-dependent protein deacetylase); this active ingredient may, for example, be resveratrol or in suitable formulations, or those compounds as specified in WO2007019416 (e.g. SRT-1720).

In one embodiment of the invention, the further active ingredient is DM-71 (N-acetyl-L-cysteine with bethanechol).

In one embodiment, the compound of the formula I is administered in combination with antihypercholesterolemic compounds, as described, for example, in WO2007107587, WO2007111994.

In another embodiment, the compound of the formula I is administered in combination with a cyclic peptide agonist of the VPAC2 receptor, as described, for example, in WO2007101146, WO2007133828.

In a further embodiment, the compound of the formula I is administered in combination with an agonist of the endothelin receptor, as described, for example, in WO2007112069.

In a further embodiment, the compound of the formula I is administered in combination with AKP-020 (bis(ethylmaltolato)oxovanadium(IV)).

In another embodiment, the compound of the formula I is administered in combination with tissue-selective androgen receptor modulators (SARM), as described, for example, in WO2007099200.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In another embodiment of the invention, the further active ingredient is metreleptin (recombinant methionyl-leptin) combined with pramlintide.

In a further embodiment of the invention, the further active ingredient is the tetrapeptide ISF-402.

In one embodiment, the further active ingredient is dexamphetamine or amphetamine.

In one embodiment, the further active ingredient is fenfluramine or dexfenfluramine.

In another embodiment, the further active ingredient is sibutramine.

In one embodiment, the further active ingredient is mazindol or phentermin.

In a further embodiment, the further active ingredient is geniposidic acid (WO2007100104).

In one embodiment, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can also be administered in the form of food products such as, for example, in bakery products or muesli bars.

It will be appreciated that every suitable combination of the compounds of the invention with one or more of the aforementioned compounds and optionally one or more other pharmacologically active substances is considered to be covered by the scope of protection conferred by the present invention.

FM-VP4
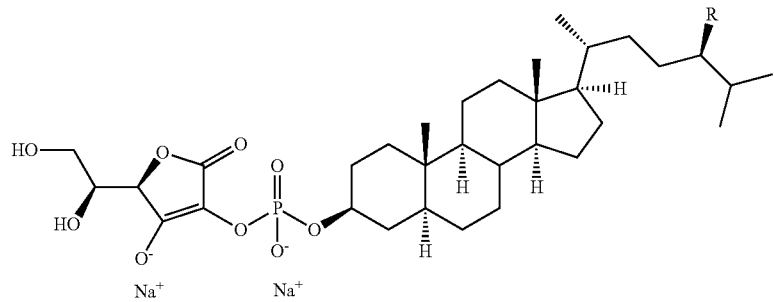
R = CH₃; CH₂—CH₃
JTT-501
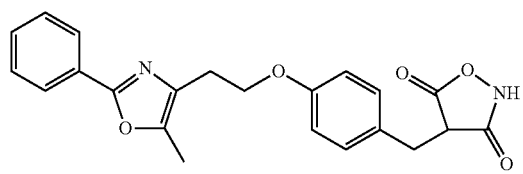
GI 262570
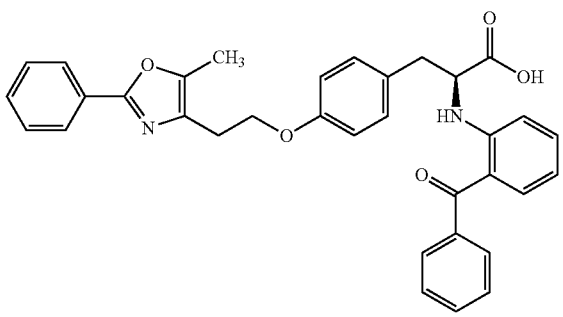
CS-011
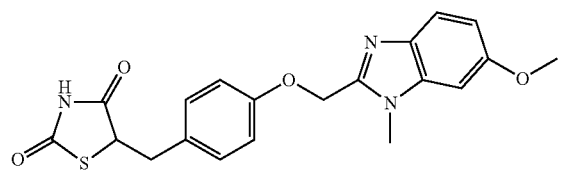
Rivoglitazone
GW-9578
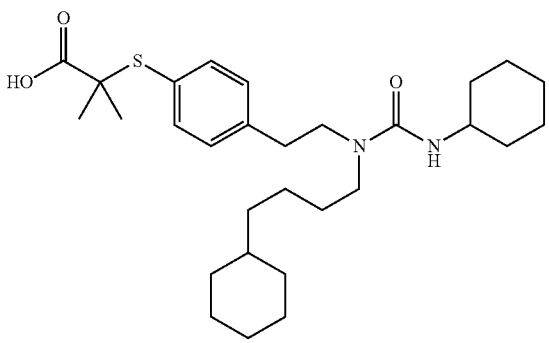
K-111
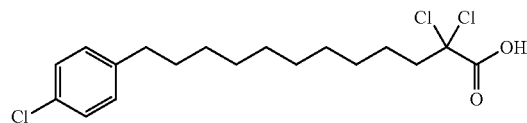
LY-518674
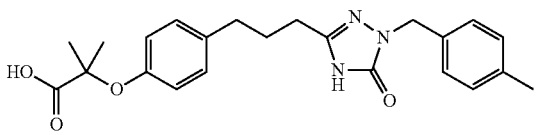
KRP-101
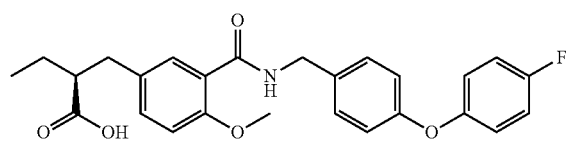
LY-510929
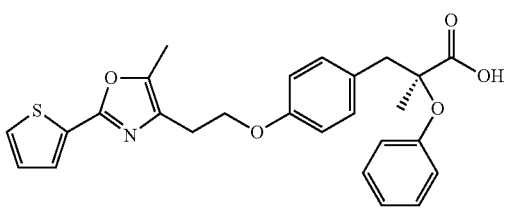

-continued
GW-501516
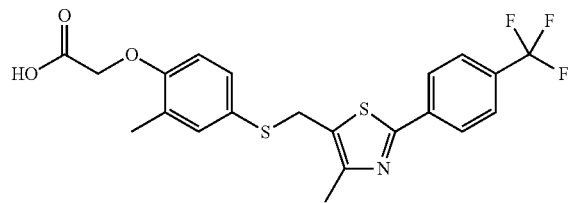
BMS-201038
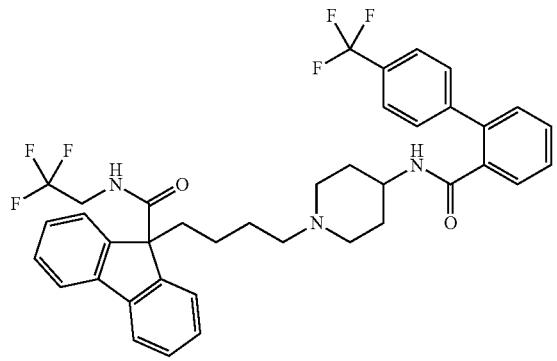
R-103757
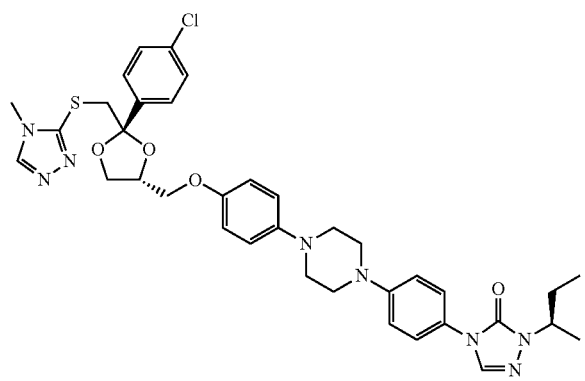
JTT-705
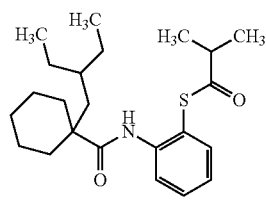
OPC-14117
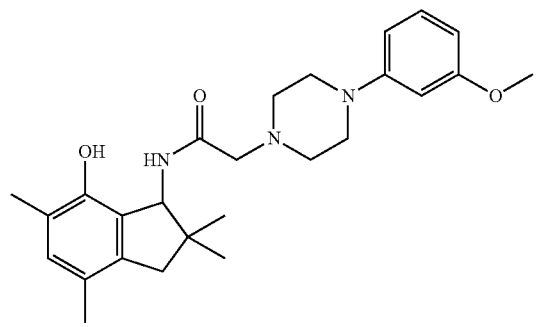
NO-1886
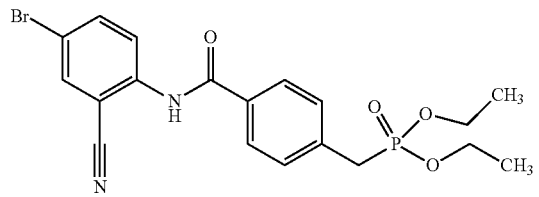
SB-204990
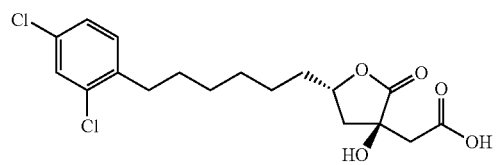
BMS-188494
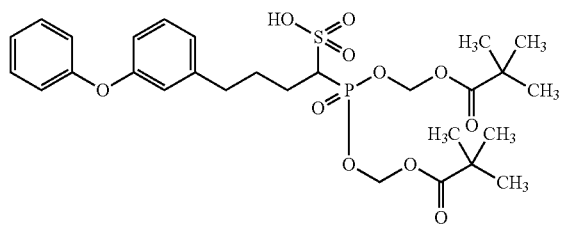
CI-1027
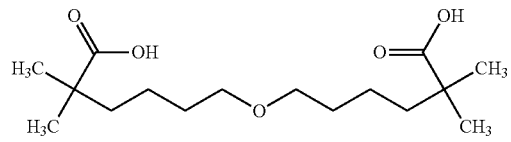
ATL-962
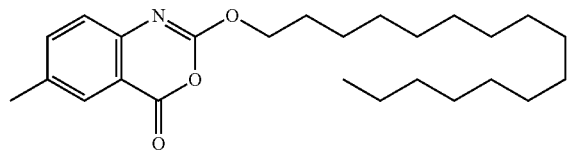

-continued
FR-258900
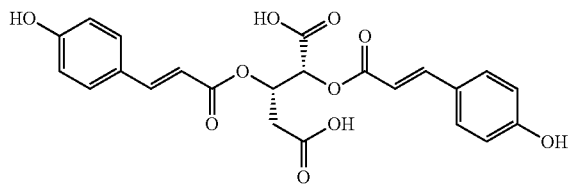
NNC-25-2504
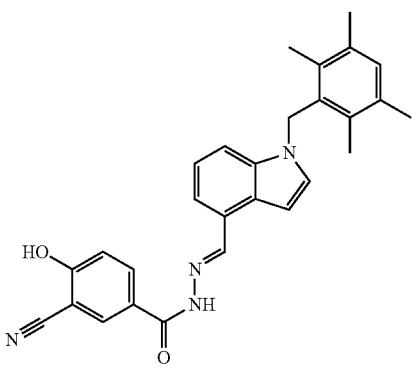
LY-2121260
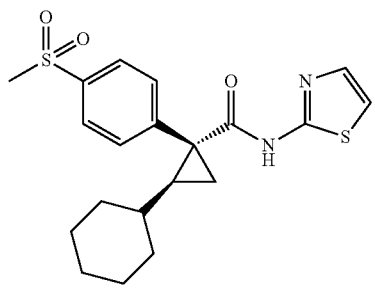
GKA-50
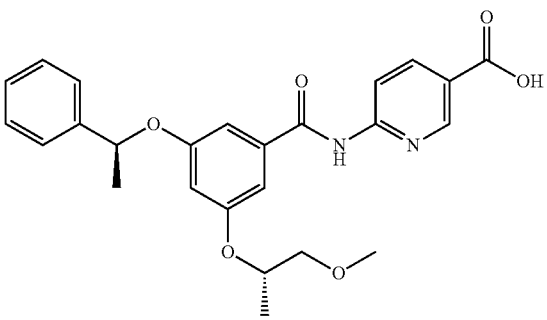
FR-225654
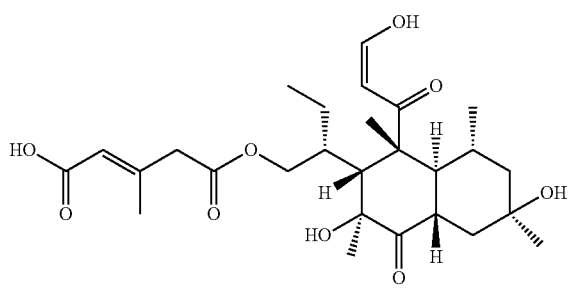
KST-48
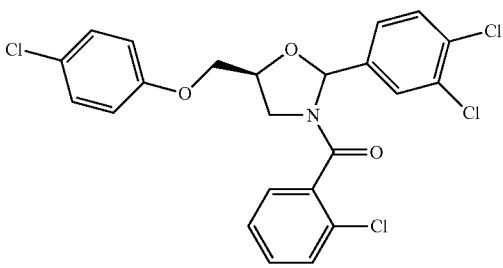
BMS-477118
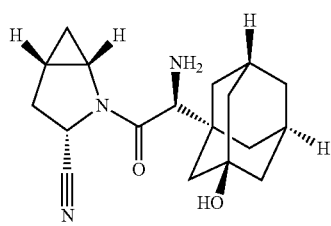
BVT-2733
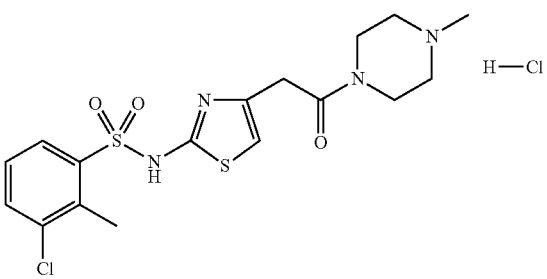
T-1095
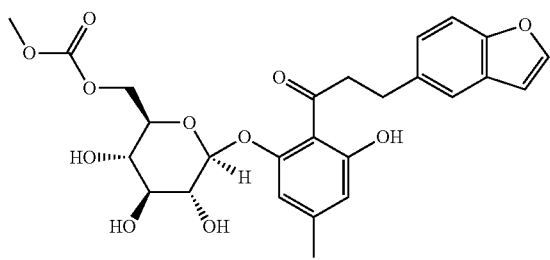
SPP-301
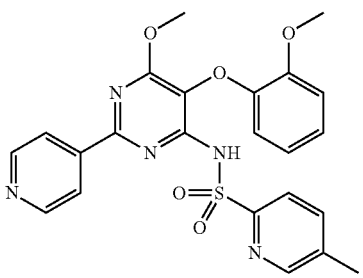

27
THIQ
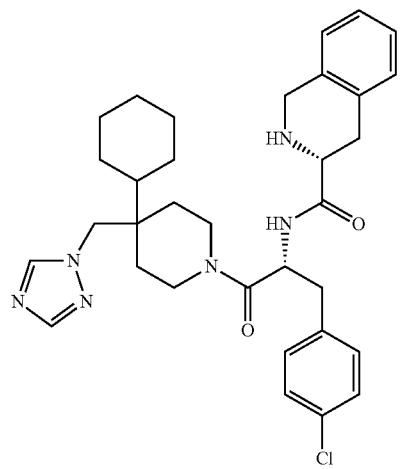
28
MB243
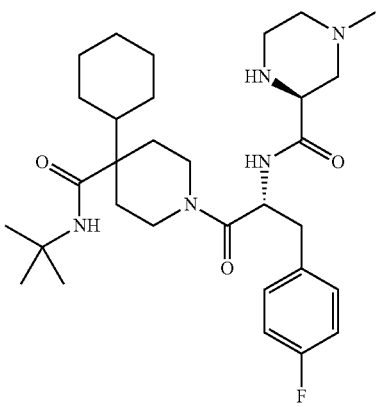
RY764
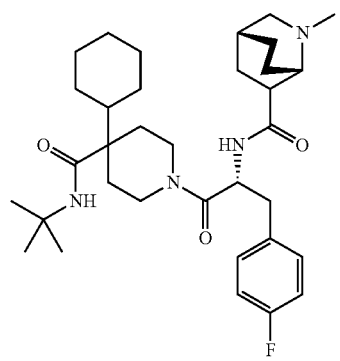
CHIR-785
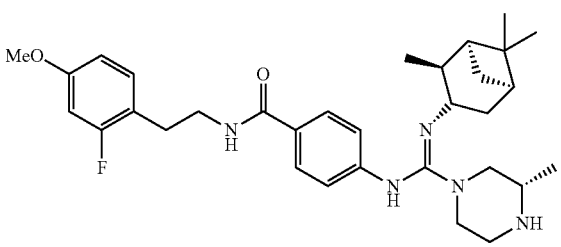
A-761
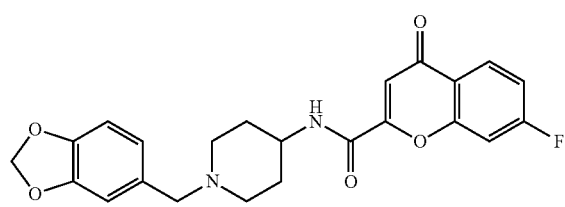
A-665798
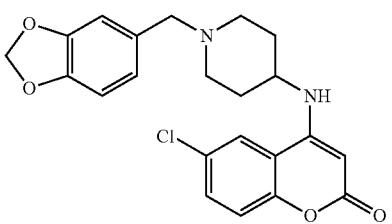
ATC-0175
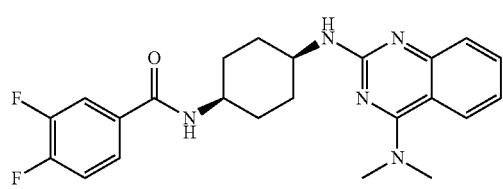
T-226296
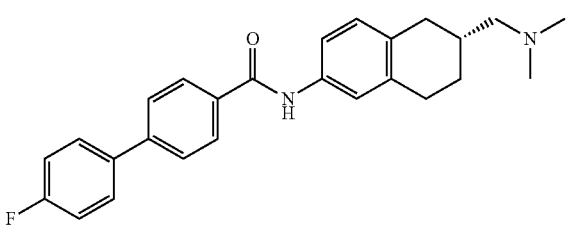
GW-803430
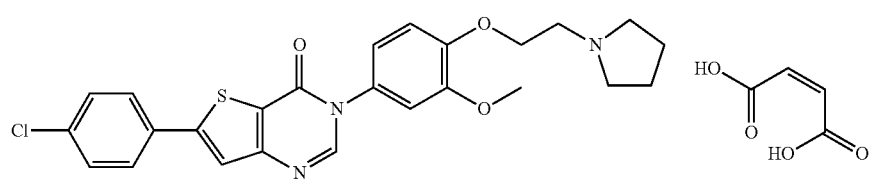

AOD-9604
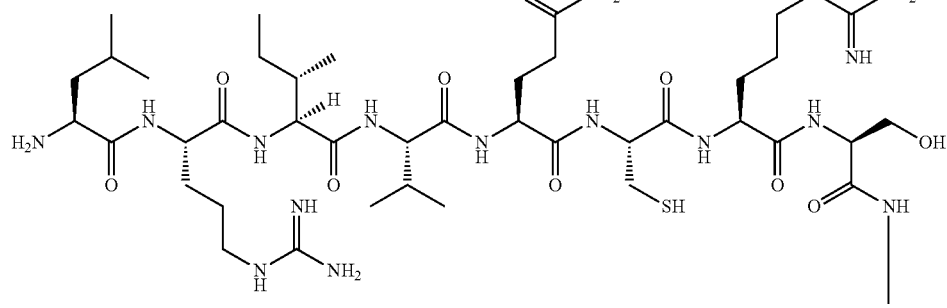
A-778193
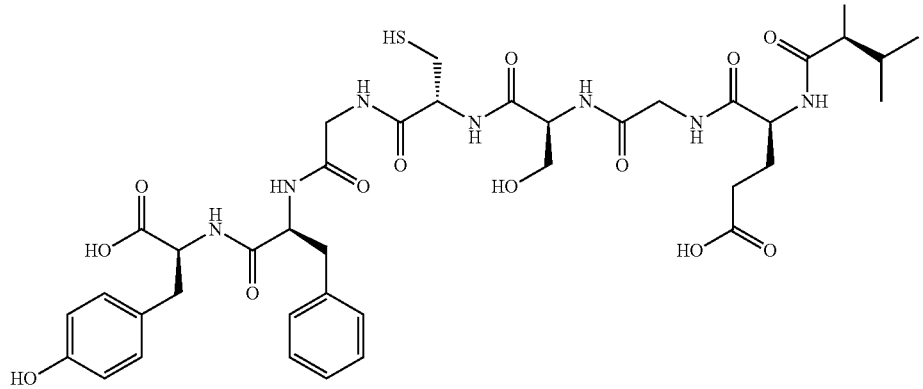
C75
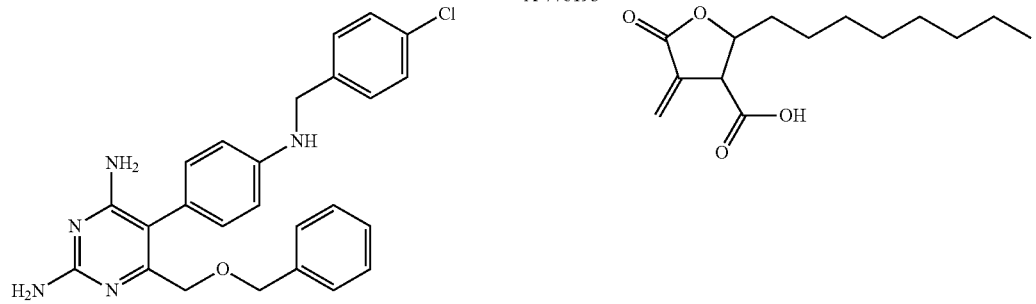
Oleoyl-Estrone
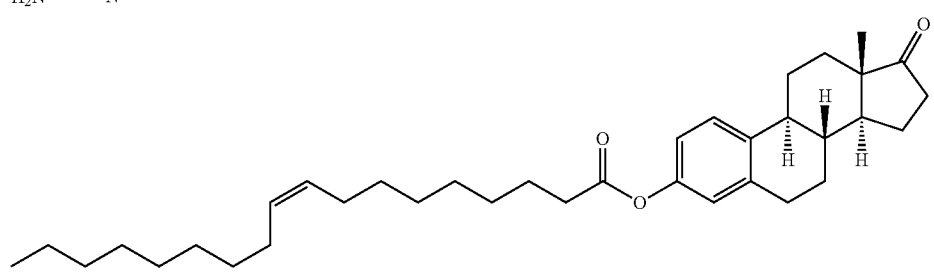
KB-2115
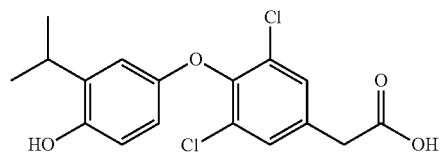
KCP-265
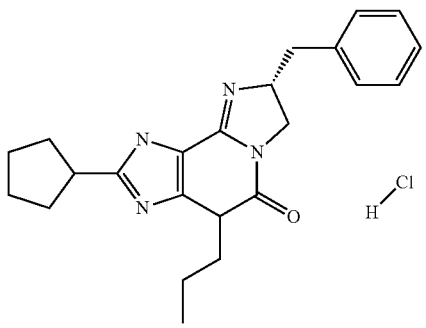

-continued
SMP-797
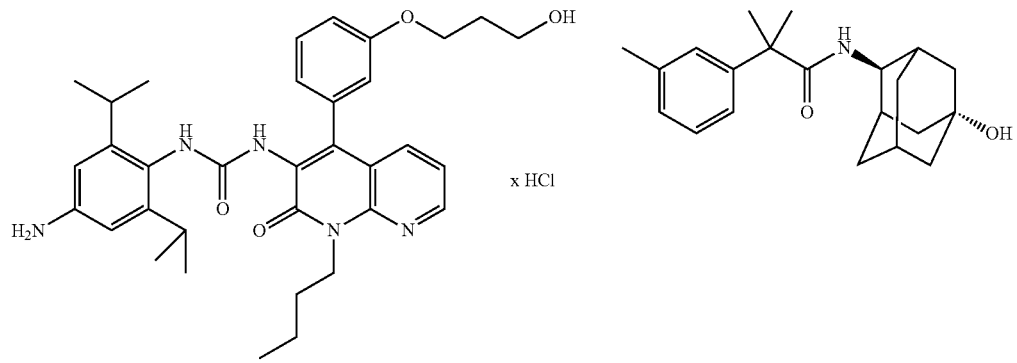
JNJ-25918646
PSN-632408
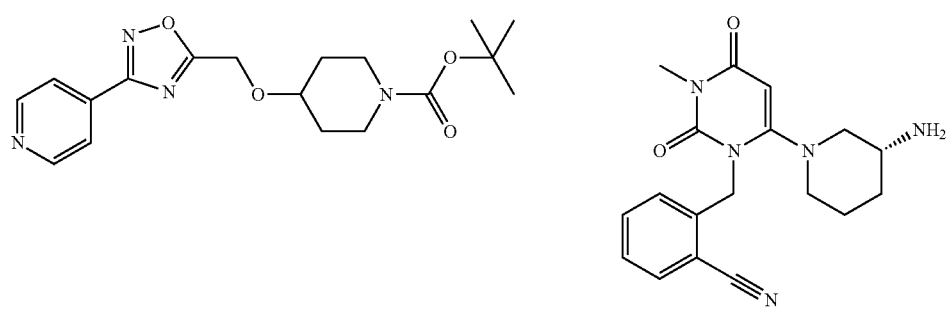
SYR-322
DP-893
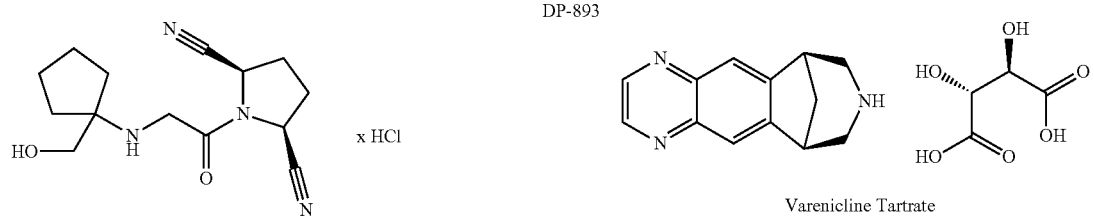
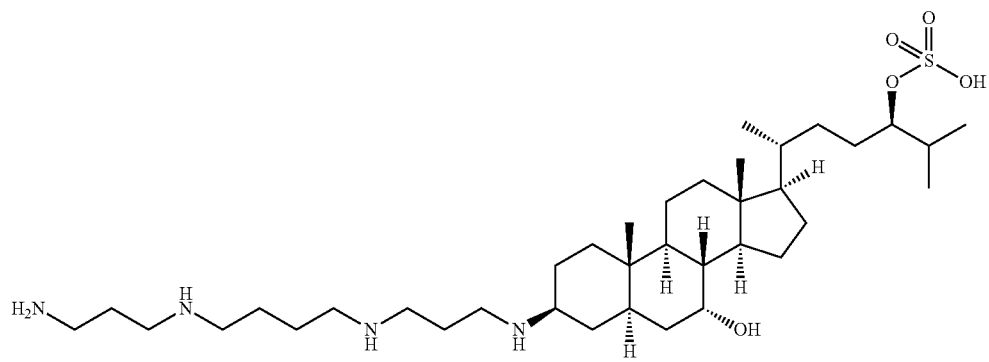
Trodusquemine
Varenicline Tartrate
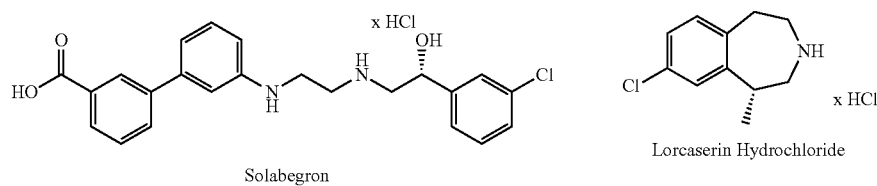
Solabegron
Lorcaserin Hydrochloride -continued
L-152804
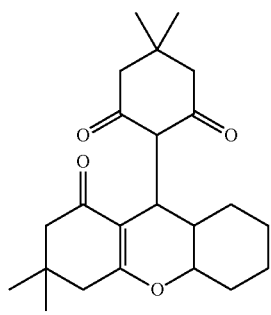
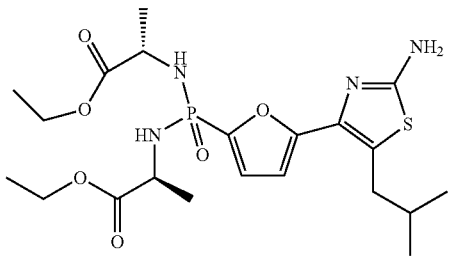
MB-06322
CS-917
N-5984
BIM-51077
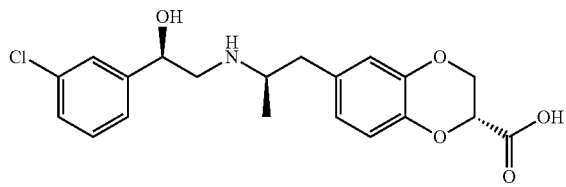
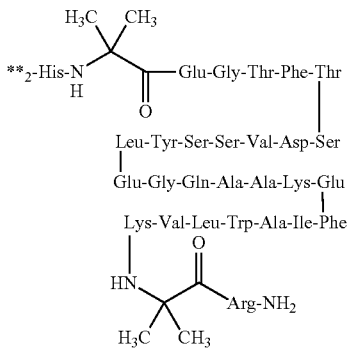
TAK-536
E-6837
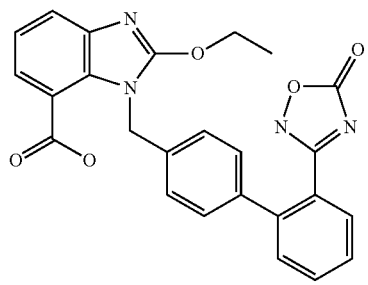
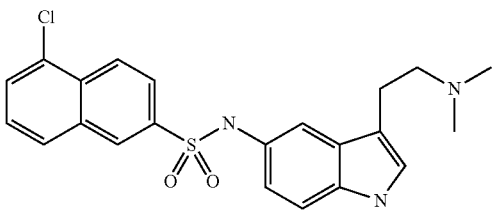
BVT-74316
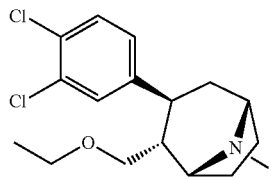
Tesofensine
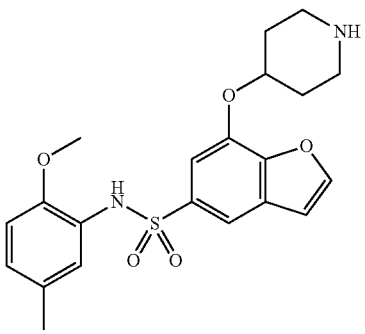
ABT-341
MK-0364
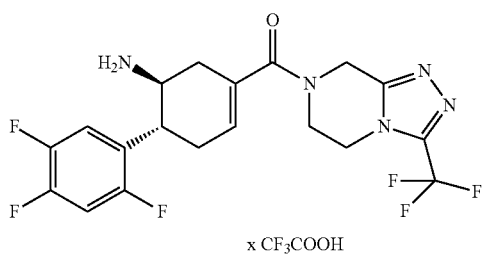
x CF$_3$COOH
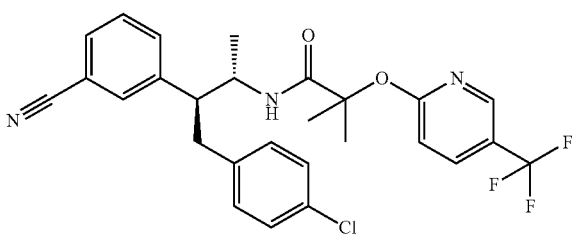

-continued
ABT-279
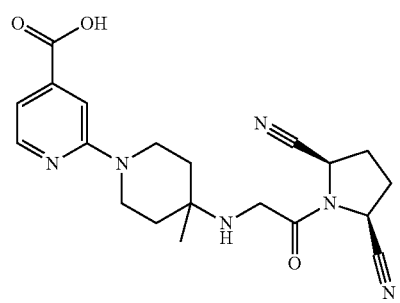
x 2 CF₃COOH
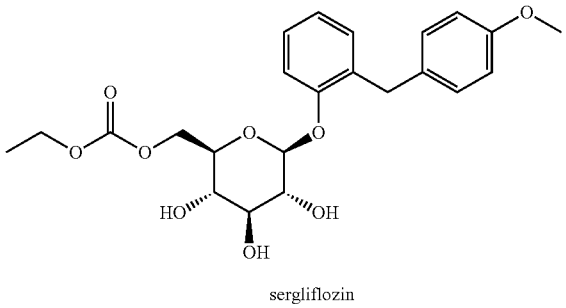
sergliflozin
SLV-319
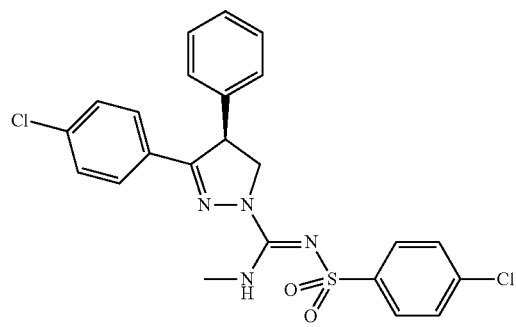
TAK-475
AVE 1625
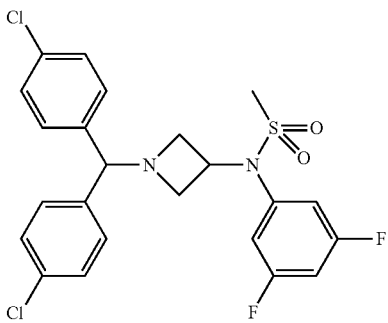
AS-1552133
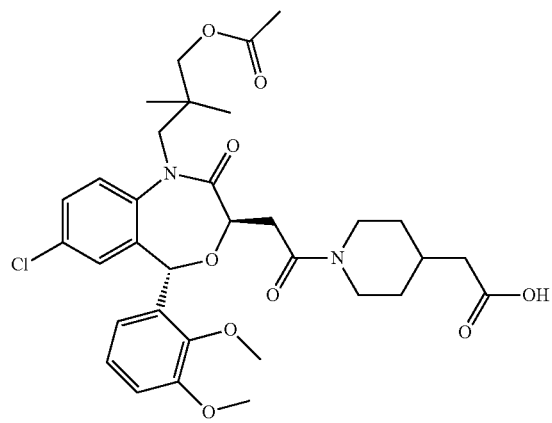
(Lapaquistat Acetate)
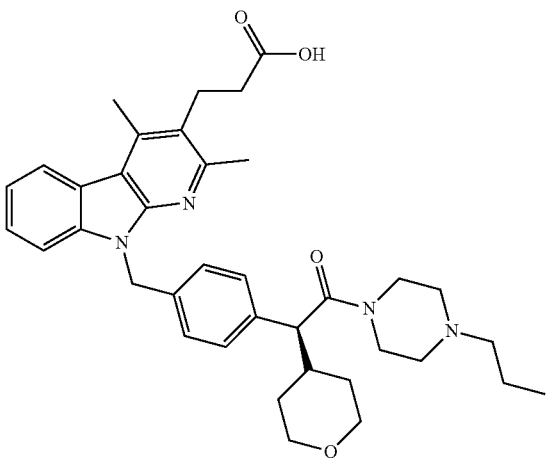
MB-07344
CKD-501
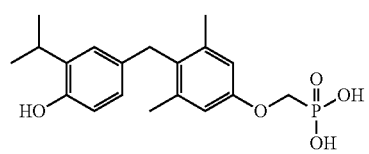
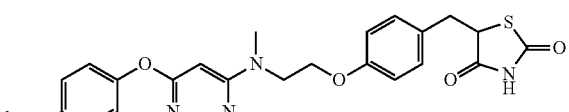
x H₂SO₄
(Lobeglitazone Sulfate)
MB-07811
JMV-2959
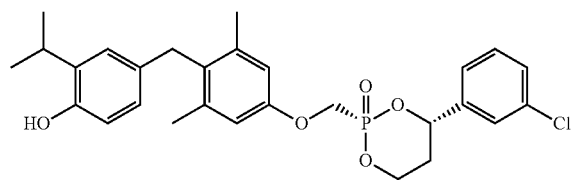
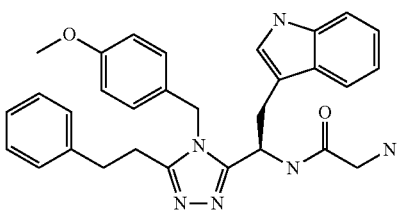

-continued
JMV-3002
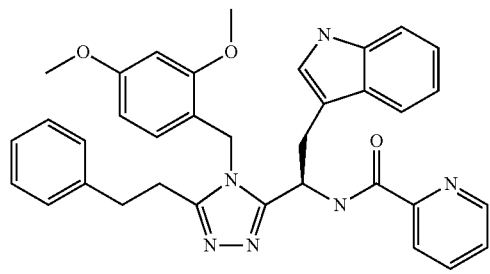
JMV-2810
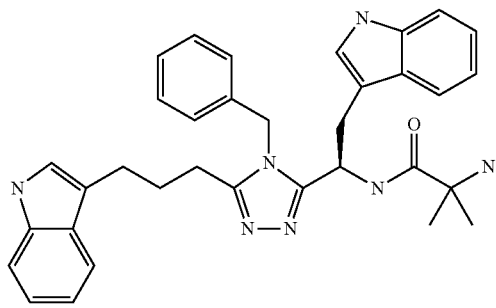
JMV-2951
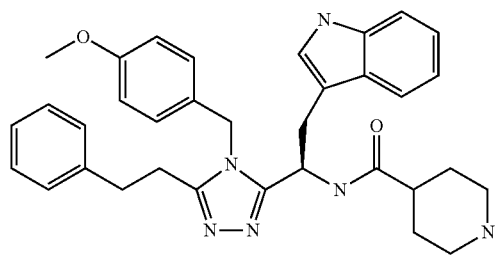
BMS-309403
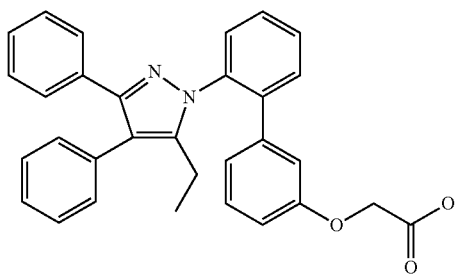
PSN-119-1
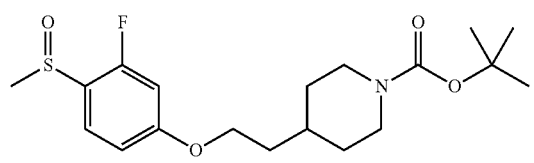
S-40755
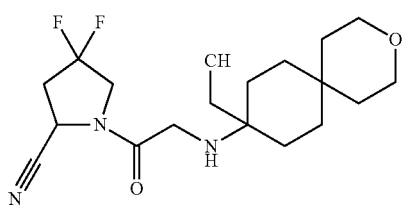
LY-2463665
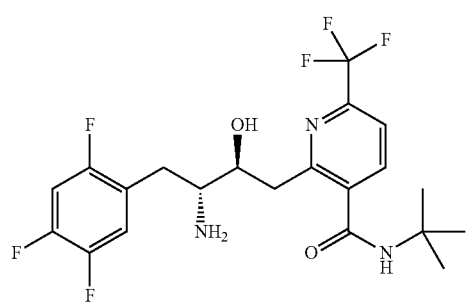
BMS-512148
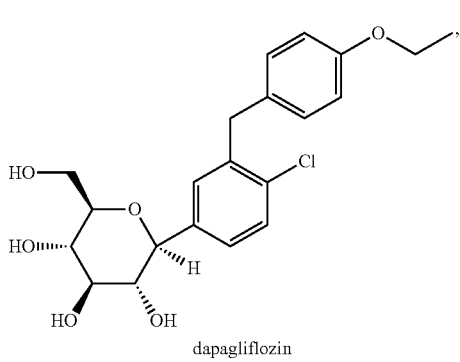
dapagliflozin
BI-1356
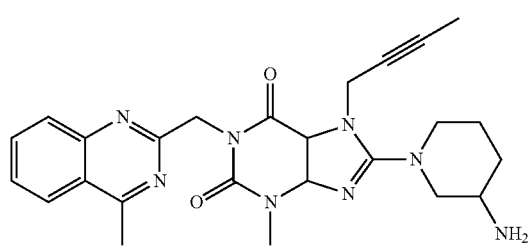
PF-429242
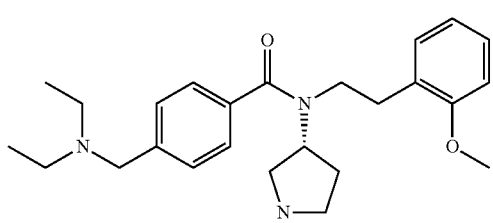

-continued
SLV-348
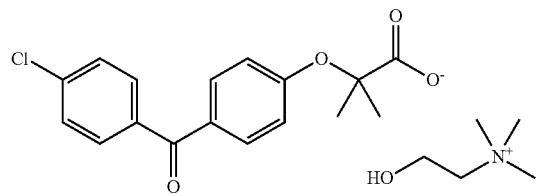
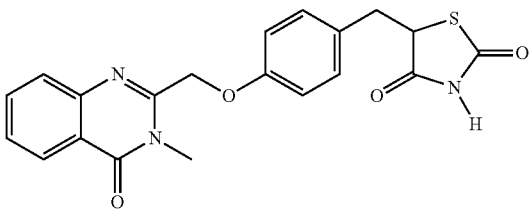
balaglitazone
"NPY-5-BY"
BMS-711939
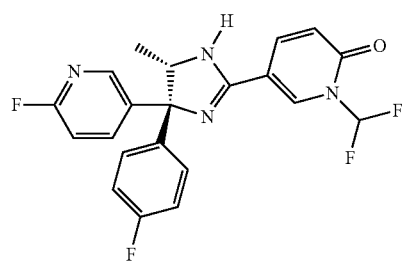
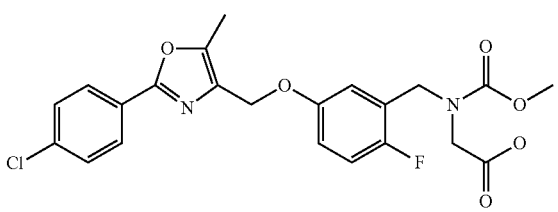
BMS-687453
ST-3473
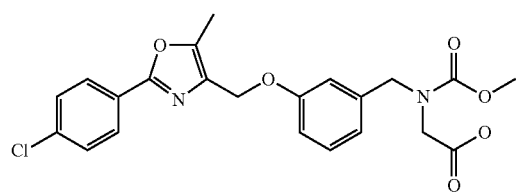
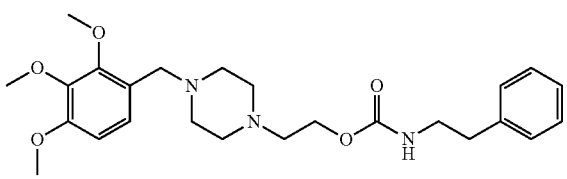
DOV-21947
DM-71
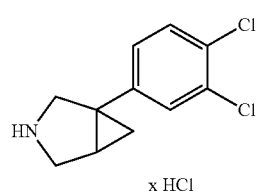
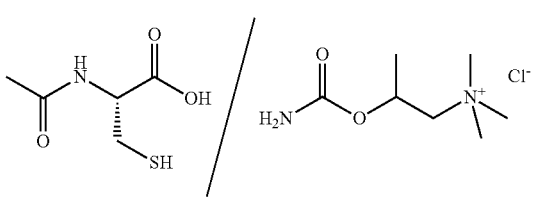
x HCl
AEGR-733
KY-382
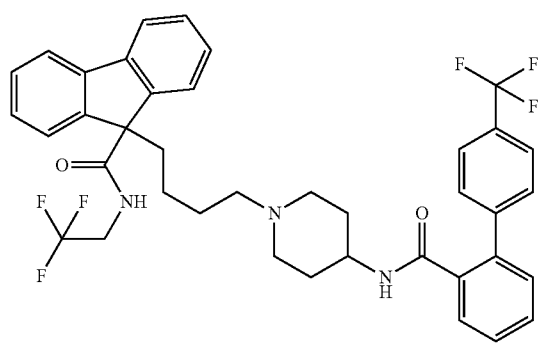
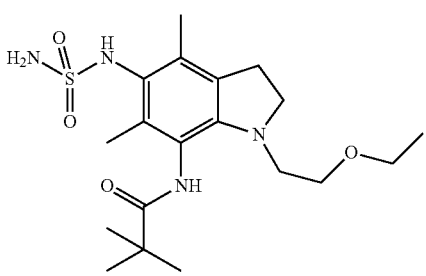
YIL-781
YIL-870
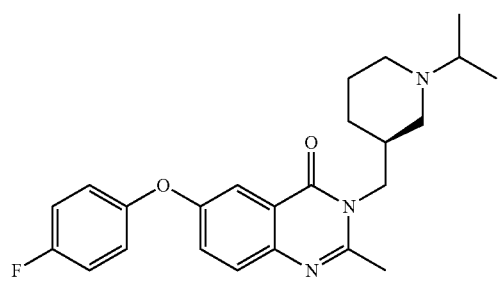

-continued

PRX-07034

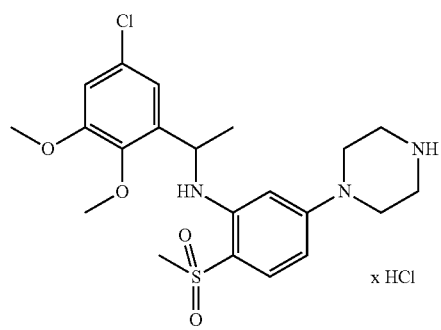

x HCl

PF-00389027

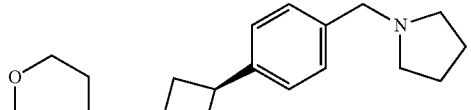

KB-3305

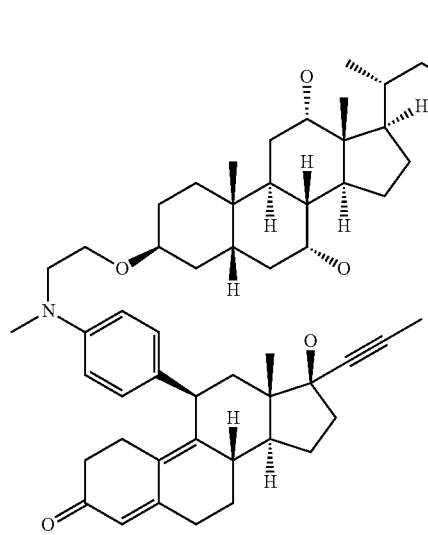

ISF-402

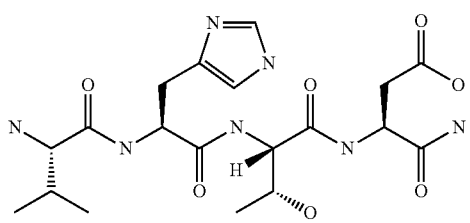

SRT-1720

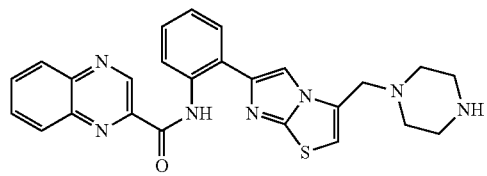

darapladib

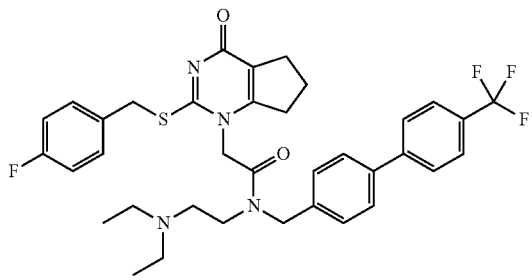

A-002

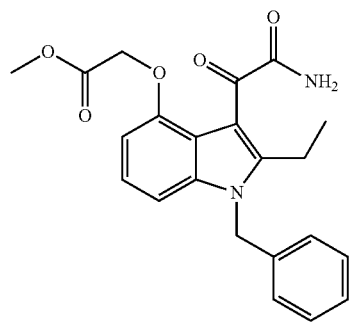

DITPA

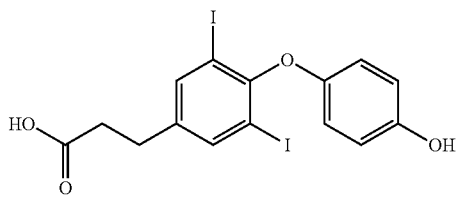

EXAMPLES

The examples and preparation methods adduced below serve to illustrate the invention, but without limiting it.

The inventive compounds of the formula I can be prepared with the aid of reactions known in principle. For example, the compounds were prepared according to the general reaction schemes which follow.

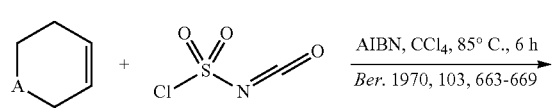

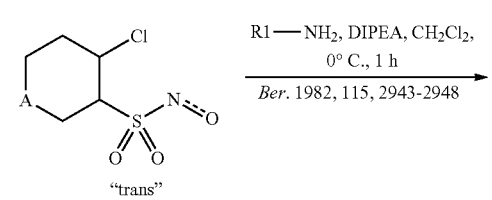

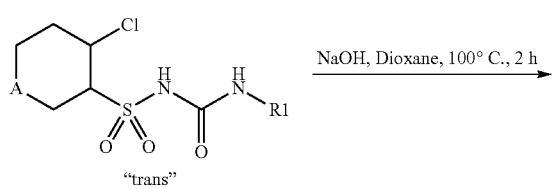

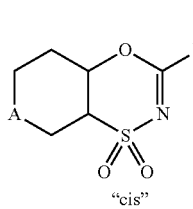

A cyclic alkene can be used to prepare a corresponding chlorosulfonyl isocyanate in a free-radical reaction. This gives exclusively the cis configuration. Subsequently, reaction is effected with primary amines to give chlorosulfonylureas. The corresponding sodium salts cyclize when heated to give cis-4,4-dioxooxathiazines.

In the cases in which diastereomers or racemates form during the synthesis, these can be separated from one another by preparative HPLC.

Some of the primary amines used are commercially available. Other primary amines used were prepared as outlined by way of example in the scheme which follows.

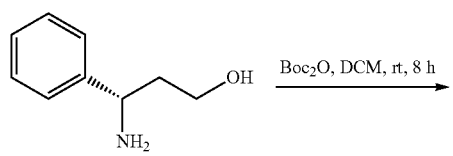

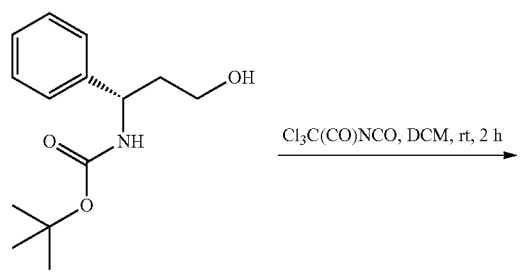

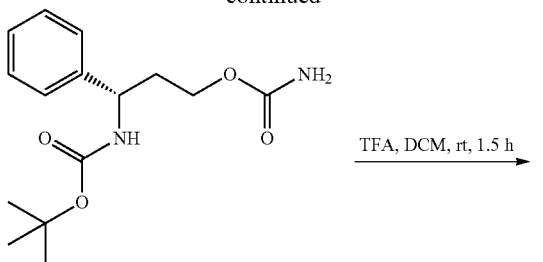

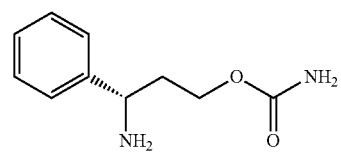

Others among the primary amines used were prepared as outlined by way of example in the scheme which follows.

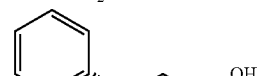

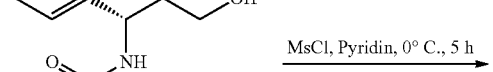

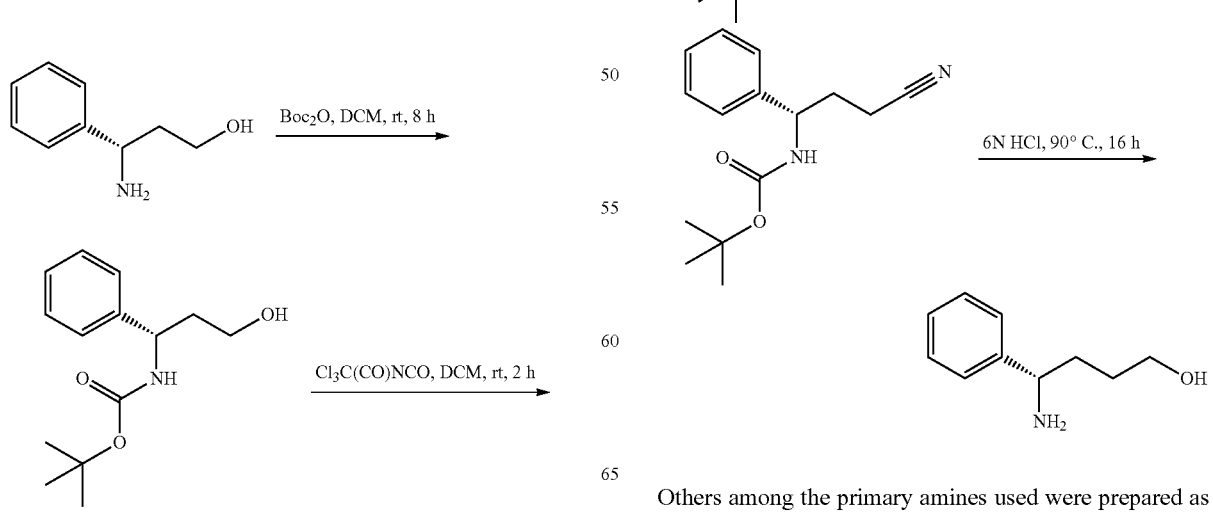

Others among the primary amines used were prepared as outlined by way of example in the scheme which follows.

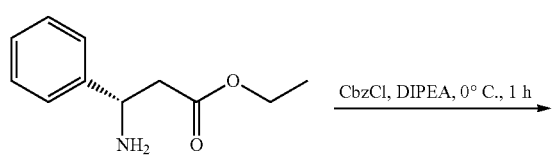
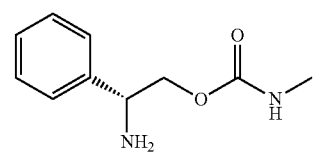
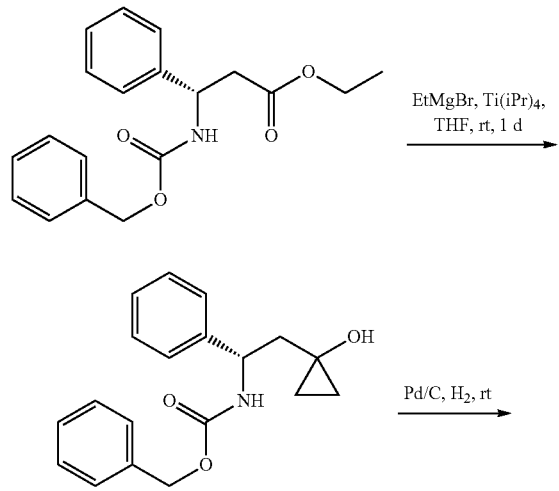
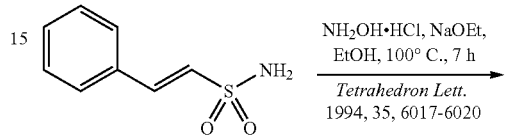
Others among the primary amines used were prepared as outlined by way of example in the scheme which follows.
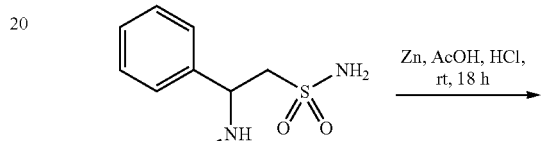
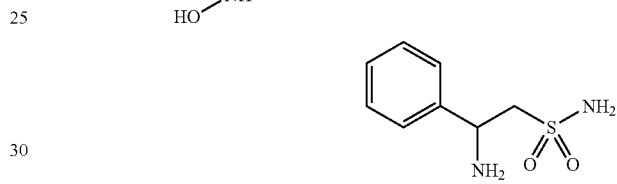
Other inventive compounds can be obtained in other ways outlined by way of example in the scheme which follows.
Others among the primary amines used were prepared as outlined by way of example in the scheme which follows.
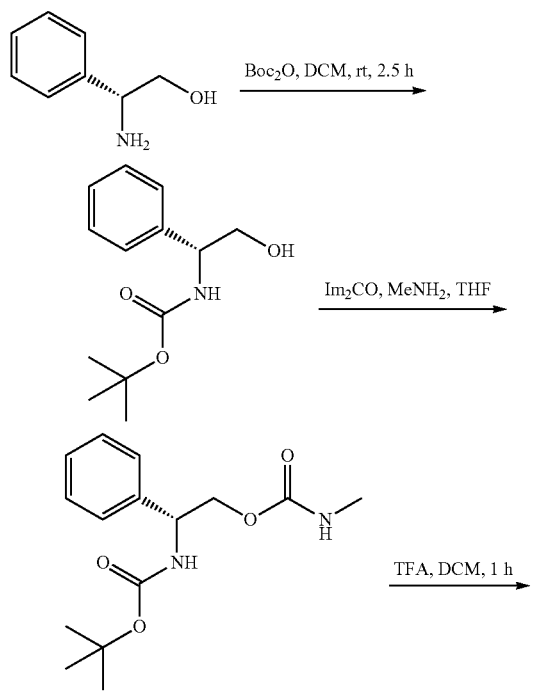
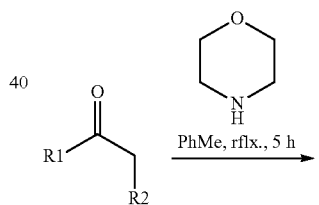
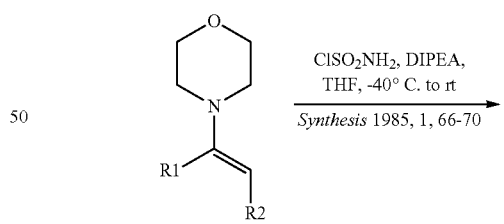
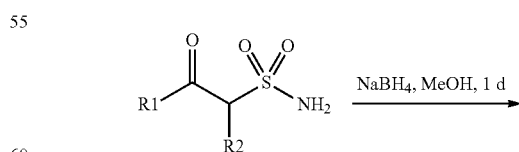
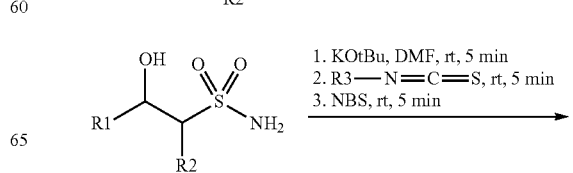

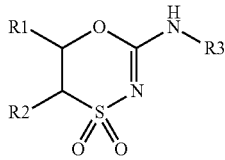

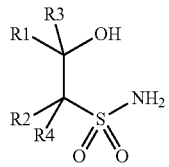

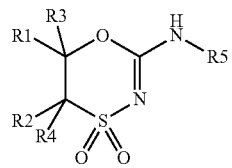

A ketone is reacted with morpholine to give the enamine. The latter is then treated with sulfamoyl chloride. The resulting ketosulfonamide can be reduced with a suitable reducing agent, for example sodium borohydride, to give the hydroxysulfonamide. This forms diastereomers and, in the case of cyclic ketones, cis/trans isomers, which can be separated from one another. The ratio of the diastereomers or cis/trans isomers depends on the nature of the R1 and R2 radicals and on the choice of reducing agent. The treatment of the hydroxysulfonamide with base and an isothiocyanate, and subsequent oxidative ring closure with NBS, gives the desired 4,4-dioxooxathiazines.

The isothiocyanates used are obtained by the reaction of a primary amine with thiocarbonyldiimidazole, in which case any troublesome functional groups present, for example hydroxyl groups, have been blocked with suitable protecting groups, for example silyl ethers. The protecting groups are removed at the end of the sequence by suitable methods, for example silyl groups by treatment with methanolic hydrochloric acid.

In the cases in which diastereomers or racemates form during the synthesis, these can be separated from one another by preparative HPLC.

Other inventive compounds can be obtained in other ways outlined by way of example in the scheme which follows.

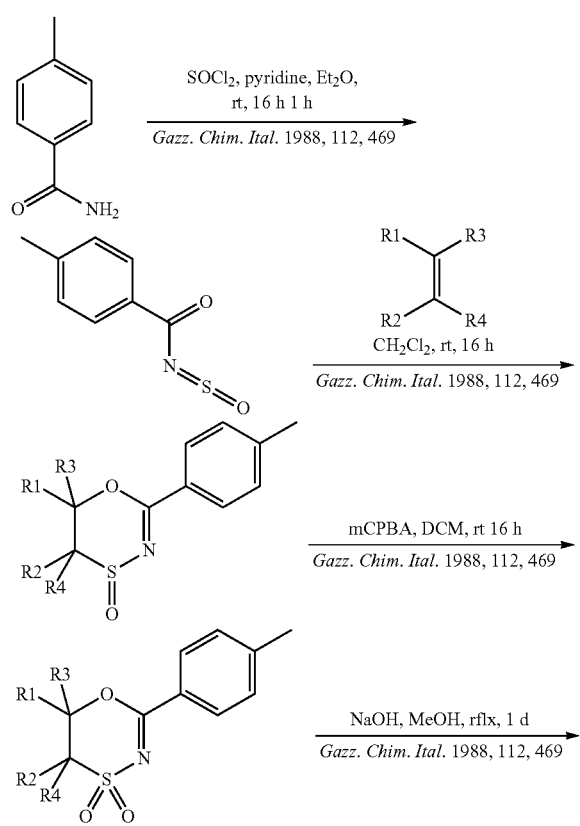

4-Tolylamide is reacted with thionyl chloride and pyridine to give N-sulfinyl-4-tolylamide. The latter reacts in a hetero-Diels-Alder reaction with an alkene to give 2-tolyl-4-oxathiazine. In the case of cyclic alkenes, exclusively the cis configuration is obtained. After oxidation to give 2-tolyl-4,4-dioxathiazine with 3-chloroperbenzoic acid, hydrolysis is effected with sodium hydroxide solution to give 1,2-dimethyl-2-hydroxycyclohexylsulfonamide. Further treatment with base and an isothiocyanate, and subsequent oxidative ring closure with NBS gives the desired 4,4-dioxooxathiazines.

In the cases in which diastereomers or racemates form during the synthesis, these can be separated from one another by preparative HPLC.

Other examples again were obtained as indicated in the following scheme:

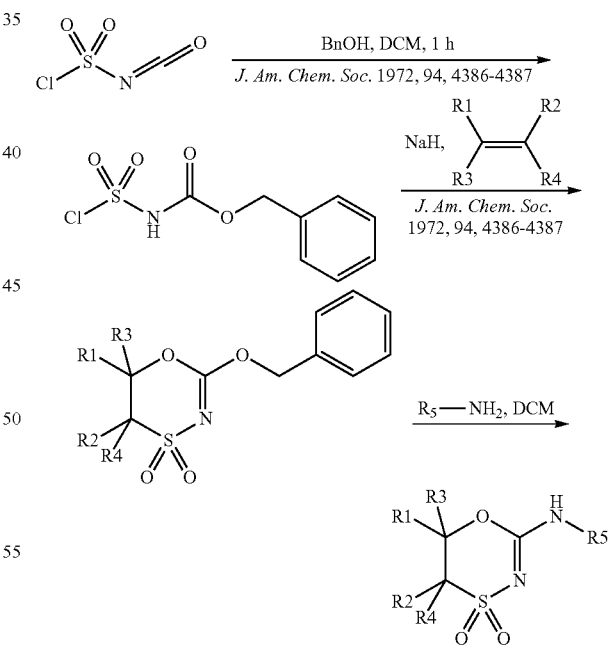

Chlorosulfonyl isocyanate is first reacted with benzyl alcohol to give the corresponding chlorosulfonyl carbamate. The latter reacts in a 2+4 cycloaddition with an alkene to give the corresponding 2-(benzyloxy)-4,4-dioxothiazine. In the case of cyclic alkenes, exclusively the cis configuration is obtained. The reaction with amines affords the desired 4,4-dioxooxathiazines.

If the amines used contain the desired functional groups in masked form, these are converted to the desired functionalities by suitable processes. For example, an ester can be converted to an alcohol by the reaction with DIBAL-H and then NaBH$_4$.

In the cases in which diastereomers or racemates form during the synthesis, these can be separated from one another by preparative HPLC.

The examples adduced below serve to illustrate the invention, but without restricting it.

TABLE 1

| Example | CHEMISTRY | Method | Retention time | Molar mass (g/mol) | Name |
|---|---|---|---|---|---|
| 1 | 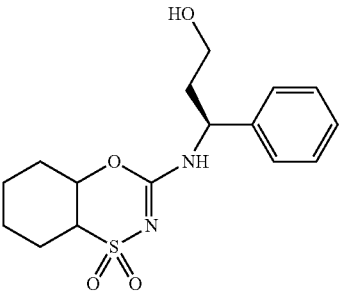 [SMILES: O=S1(=O)N=C(N[C@@H](CCO)c2ccccc2)OC2CCCCC21] | A | 1.052 | 338.4 | (S)-3-(−1,1-Dioxo-4a,5,6,7,8,8a-hexahydro-1H-1lambda6-benzo[1,4,3]oxathiazin-3-ylamino)-3-phenyl-propan-1-ol |
| 2 | 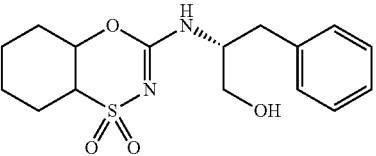 [SMILES: O=S1(=O)N=C(N[C@@H](CO)Cc2ccccc2)OC2CCCCC21] | G | 1.26 | 338.4 | (R)-2-(−1,1-Dioxo-4a,5,6,7,8,8a-hexahydro-1H-1lambda6-benzo[1,4,3]oxathiazin-3-ylamino)-3-phenyl-propan-1-ol |
| 3 | 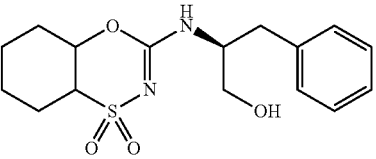 [SMILES: O=S1(=O)N=C(N[C@H](CO)Cc2ccccc2)OC2CCCCC21] | J | 2.63 | 338.4 | (S)-2-(−1,1-Dioxo-4a,5,6,7,8,8a-hexahydro-1H-1lambda6-benzo[1,4,3]oxathiazin-3-ylamino)-3-phenyl-propan-1-ol |
| 4 | 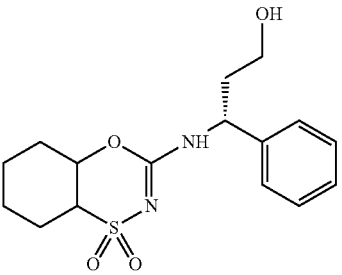 [SMILES: O=S1(=O)N=C(N[C@H](CCO)c2ccccc2)OC2CCCCC21] | K | 1.83 | 338.4 | (R)-3-(−1,1-Dioxo-4a,5,6,7,8,8a-hexahydro-1H-1lambda6-benzo[1,4,3]oxathiazin-3-ylamino)-3-phenyl-propan-1-ol |
| 5 | 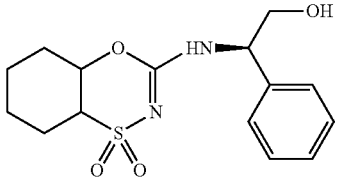 [SMILES: O=S1(=O)N=C(N[C@@H](CO)c2ccccc2)OC2CCCCC21] | K | 1.83 | 324.4 | (R)-2-(−1,1-Dioxo-4a,5,6,7,8,8a-hexahydro-1H-1lambda6-benzo[1,4,3]oxathiazin-3-ylamino)-2-phenyl-ethanol |
| 6 | 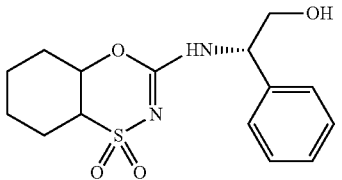 [SMILES: O=S1(=O)N=C(N[C@H](CO)c2ccccc2)OC2CCCCC21] | K | 1.83 | 324.4 | (S)-2-(−1,1-Dioxo-4a,5,6,7,8,8a-hexahydro-1H-1lambda6-benzo[1,4,3]oxathiazin-3-ylamino)-2-phenyl-ethanol |

TABLE 1-continued

| Example | CHEMISTRY | Method | Retention time | Molar mass (g/mol) | Name |
|---|---|---|---|---|---|
| 7 | | K | 1.88 | 367.4 | Carbamic acid (S)-2-(−1,1-dioxo-4a,5,6,7,8,8a-hexahydro-1H-1lambda6-benzo[1,4,3]oxathiazin-3-ylamino)-2-phenyl-ethyl ester |
| 8 | | K | 1.88 | 367.4 | Carbamic acid (R)-2-(−1,1-dioxo-4a,5,6,7,8,8a-hexahydro-1H-1lambda6-benzo[1,4,3]oxathiazin-3-ylamino)-2-phenyl-ethyl ester |
| 9 | | A | 1.115 | 356.4 | (S)-3-(−1,1-Dioxo-4a,5,6,7,8,8a-hexahydro-1H-1lambda6-benzo[1,4,3]oxathiazin-3-ylamino)-3-(4-fluoro-phenyl)-propan-1-ol |
| 10 | | A | 1.116 | 356.4 | (S)-3-(−1,1-Dioxo-4a,5,6,7,8,8a-hexahydro-1H-1lambda6-benzo[1,4,3]oxathiazin-3-ylamino)-3-(3-fluoro-phenyl)-propan-1-ol |
| 11 | | D | 4.572 | 338.4 | (−)-(S)-3-(1,1-Dioxo-4a,5,6,7,8,8a-hexahydro-1H-1lambda6-benzo[1,4,3]oxathiazin-3-ylamino)-3-phenyl-propan-1-ol * |
| 12 | | D | 6.813 | 338.4 | (−)-(S)-3-(1,1-Dioxo-4a,5,6,7,8,8a-hexahydro-1H-1lambda6-benzo[1,4,3]oxathiazin-3-ylamino)-3-phenyl-propan-1-ol * |

TABLE 1-continued

| Example | CHEMISTRY | Method | Retention time | Molar mass (g/mol) | Name |
|---|---|---|---|---|---|
| 13 | | K | 1.89 | 352.4 | (R)-4-(−1,1-Dioxo-4a,5,6,7,8,8a-hexahydro-1H-1lambda6-benzo[1,4,3]oxathiazin-3-ylamino)-4-phenyl-butan-1-ol |
| 14 | | K | 1.88 | 352.4 | (S)-4-(−1,1-Dioxo-4a,5,6,7,8,8a-hexahydro-1H-1lambda6-benzo[1,4,3]oxathiazin-3-ylamino)-4-phenyl-butan-1-ol |
| 15 | | I | 6.139 | 382.4 | 1-[(S)-2-(1,1-Dioxo-4a,5,6,7,8,8a-hexahydro-1H-1lambda6-benzo[1,4,3]oxathiazin-3-ylamino)-2-(4-fluoro-phenyl)-ethyl]-cyclopropanol * |
| 16 | | I | 6.993 | 382.4 | 1-[(S)-2-(1,1-Dioxo-4a,5,6,7,8,8a-hexahydro-1H-1lambda6-benzo[1,4,3]oxathiazin-3-ylamino)-2-(4-fluoro-phenyl)-ethyl]-cyclopropanol * |
| 17 | | A | 1.116 | 356.4 | (S)-3-(−1,1-Dioxo-4a,5,6,7,8,8a-hexahydro-1H-1lambda6-benzo[1,4,3]oxathiazin-3-ylamino)-3-(3-fluoro-phenyl)-propan-1-ol |
| 18 | | I | 8.807 | 356.4 | (S)-3-(−1,1-Dioxo-4a,5,6,7,8,8a-hexahydro-1H-1lambda6-benzo[1,4,3]oxathiazin-3-ylamino)-3-(4-fluoro-phenyl)-propan-1-ol * |

TABLE 1-continued

| Example | CHEMISTRY | Method | Retention time | Molar mass (g/mol) | Name |
|---|---|---|---|---|---|
| 19 | | I | 7.173 | 356.4 | (S)-3-(1,1-Dioxo-4a,5,6,7,8,8a-hexahydro-1H-1lambda6-benzo[1,4,3]oxathiazin-3-ylamino)-3-(4-fluoro-phenyl)-propan-1-ol * |
| 20 | | I | 8.832 | 356.4 | (S)-3-(1,1-Dioxo-4a,5,6,7,8,8a-hexahydro-1H-1lambda6-benzo[1,4,3]oxathiazin-3-ylamino)-3-(4-fluoro-phenyl)-propan-1-ol * |
| 21 | | I | 7.263 | 356.4 | (−)-(S)-3-(1,1-Dioxo-4a,5,6,7,8,8a-hexahydro-1H-1lambda6-benzo[1,4,3]oxathiazin-3-ylamino)-3-(3-fluoro-phenyl)-propan-1-ol * |
| 22 | | I | 9.508 | 356.4 | (−)-(S)-3-(1,1-Dioxo-4a,5,6,7,8,8a-hexahydro-1H-1lambda6-benzo[1,4,3]oxathiazin-3-ylamino)-3-(3-fluoro-phenyl)-propan-1-ol * |
| 23 | | B | 0.726 | 381.4 | Methyl-carbamic acid (R)-2-(1,1-dioxo-4a,5,6,7,8,8a-hexahydro-1H-1lambda6-benzo[1,4,3]oxathiazin-3-ylamino)-2-phenyl-ethyl ester |
| 24 | | B | 0.751 | 399.4 | Methyl-carbamic acid (R)-2-(1,1-dioxo-4a,5,6,7,8,8a-hexahydro-1H-1lambda6-benzo[1,4,3]oxathiazin-3-ylamino)-2-(4-fluoro-phenyl)-ethyl ester |

TABLE 1-continued

| Example | CHEMISTRY | Method | Retention time | Molar mass (g/mol) | Name |
|---|---|---|---|---|---|
| 25 | | B | 0.157 | 339.4 | (S)-3-((4aS,8aR)-1,1-Dioxo-4a,5,6,7,8,8a-hexahydro-1H-1lambda6-benzo[1,4,3]oxathiazin-3-ylamino)-3-pyridin-3-yl-propan-1-ol |
| 26 | | B | 0.53 | 340.4 | (S)-3-(1,1-Dioxo-5,6,8,8a-tetrahydro-1H,4aH-4,7-dioxa-1lambda6-thia-2-aza-naphthalen-3-ylamino)-3-phenyl-propan-1-ol ** |
| 27 | | B | 0.53 | 340.4 | (S)-3-(1,1-Dioxo-5,6,8,8a-tetrahydro-1H,4aH-4,7-dioxa-1lambda6-thia-2-aza-naphthalen-3-ylamino)-3-phenyl-propan-1-ol |
| 28 | | B | 0.734 | 374.4 | (S)-3-(7,7-Difluoro-1,1-dioxo-4a,5,6,7,8,8a-hexahydro-1H-1lambda6-benzo[1,4,3]oxathiazin-3-ylamino)-3-phenyl-propan-1-ol |
| 29 | | B | 0.788 | 387.5 | 2-((4aS,8aR)-1,1-Dioxo-4a,5,6,7,8,8a-hexahydro-1H-1lambda6-benzo[1,4,3]oxathiazin-3-ylamino)-2-phenyl-ethanesulfonamide * |
| 30 | | B | 0.701 | 387.5 | 2-((4aS,8aR)-1,1-Dioxo-4a,5,6,7,8,8a-hexahydro-1H-1lambda6-benzo[1,4,3]oxathiazin-3-ylamino)-2-phenyl-ethanesulfonamide * |
| 31 | | C | 2.69 | 366.5 | (S)-3-(4a,8a-Dimethyl-1,1-dioxo-4a,5,6,7,8,8a-hexahydro-1H-1lambda6-benzo[1,4,3]oxathiazin-3-ylamino)-3-phenyl-propan-1-ol * |

TABLE 1-continued

| Example | CHEMISTRY | Method | Retention time | Molar mass (g/mol) | Name |
|---------|-----------|--------|----------------|--------------------|------|
| 32 | | C | 2.68 | 366.5 | (S)-3-(4a,8a-Dimethyl-1,1-dioxo-4a,5,6,7,8,8a-hexahydro-1H-1lambda6-benzo[1,4,3]oxathiazin-3-ylamino)-3-phenyl-propan-1-ol * |
| 33 | | C | 1.88 | 367.5 | (S)-3-(4a,8a-Dimethyl-1,1-dioxo-4a,5,6,7,8,8a-hexahydro-1H-1lambda6-benzo[1,4,3]oxathiazin-3-ylamino)-3-pyridin-3-yl-propan-1-ol * |
| 34 | | C | 1.97 | 367.5 | (S)-3-(4a,8a-Dimethyl-1,1-dioxo-4a,5,6,7,8,8a-hexahydro-1H-1lambda6-benzo[1,4,3]oxathiazin-3-ylamino)-3-pyridin-3-yl-propan-1-ol * |

* isomerically pure compound
** trans compound

Chromatography Methods

Method A
   Column: YMC J'spere ODS H80, 80 Å, S-4 μm, 20×2.1 mm
   Eluent: 0 min 90% $H_2O$ (0.05% TFA)—1.9 min 95% acetonitrile—2.4 min 95% acetonitrile—2.45 min 10% acetonitrile (30° C., flow rate 1 ml/min)

Method B
   Column: Mercury MS, Luna C18(2), S-3 μm, 10×2.0 mm
   Eluent: 0 min 93% $H_2O$ (0.05% TFA)—1.2 min 95% acetonitrile—1.4 min 95% acetonitrile—1.45 min 7% acetonitrile (30° C., flow rate 1.1 ml/min)

Method C
   Column: Chiralpak AD-H/44, 5 μm, 250×4 6 mm
   Eluent: heptane:ethanol:methanol 5:1:1 (30° C., flow rate 1 ml/min)

Method D
   Column: Chiralpak AD-H/39, 5 μm, 250×4.6 mm
   Eluent: heptane:ethanol:methanol 5:1:1 (30° C., flow rate 1 ml/min)

Method E
   Column: Chiralpak AS-H/52, 5 μm, 250×4.6 mm
   Eluent: heptane:ethanol:methanol 5:1:1 (30° C., flow rate 1 ml/min)

Method F
   Column: Chiralpak AS-H/52, 5 μm, 250×4.6 mm
   Eluent: heptane:ethanol:methanol 10:1:1 (30° C., flow rate 1 ml/min)

Method G
   Column: YMC J'spere 33×2 mm 4 μM
   Eluent: 0 min 95% $H_2O$ (0.05% TFA)—2.5 min 95% acetonitrile (0.05% TFA)—3.0 min 95% acetonitrile (30° C., flow rate 1 ml/min)

Method H
   Column: Chiralpak AS-H/80, 5 μm, 250×4.6 mm
   Eluent: heptane:ethanol:methanol 2:1:1 (30° C., flow rate 1 ml/min)

Method I
   Column: Chiralpak AS-H/80, 5 μm, 250×4.6 mm
   Eluent: heptane:ethanol:methanol 6:1:1 (30° C., flow rate 1 ml/min)

Method J
   Column: YMC J'spere 33×2 mm 4 μM
   Eluent: 0 min 98% $H_2O$ (0.05% TFA)—1.0 min 98% acetonitrile (0.05% TFA)—5.0 min 95% acetonitrile—6.25 min 95% acetonitrile (30° C., flow rate 1 ml/min)

Method K
   Column: YMC J'spere 33×2 mm 4 μM
   Eluent: 0 min 95% $H_2O$ (0.05% TFA)—0.5 min 95% acetonitrile (0.05% TFA)—3.5 min 95% acetonitrile—4.0 min 95% acetonitrile (30° C., flow rate 1 ml/min)

Method L
   Column: YMC J'spere ODS H80, 80 Å, S-4 μm, 20×2.1 mm
   Eluent: 0 min 96% $H_2O$ (0.05% TFA)—2.0 min 95% acetonitrile—2.4 min 95% acetonitrile—2.45 min 4% acetonitrile (30° C., flow rate 1 ml/min)

Method M
   Column: Chiralpak AS-H/52, 5 μm, 250×4.6 mm
   Eluent: heptane:ethanol:methanol 10:1:1, preconditioned with TFA (30° C., flow rate 1 ml/min)

Method N
   Column: Chiralpak AD-H/44, 5 μm, 250×4.6 mm
   Eluent: heptane:ethanol:methanol 15:1:1, preconditioned with TFA (30° C., flow rate 1 ml/min)

Method C

Column: Waters XBridge C18, 5 µm, 250×4.6 mm

Eluent: 0 min-0.3 min 95% $H_2O$ (0.05% TFA)+5% acetonitrile (0.05% TFA)-3.5 min 95% acetonitrile (0.05% TFA)-4 min 95% acetonitrile (0.05% TFA) (30° C., flow rate 1 ml/min)

The efficacy of the compounds was tested as follows:

Enzymatic 11beta-HSD1 test:

To measure the activity of the compounds, an SPA-based detection method (Solly et al. 2005) was employed. First of all, 20 µl of the human 11β-HSD1 microsome fraction (0.2 µg of protein), prepared in 50 mM HEPES, 0.1% BSA (w/v), were applied to a plate with 384 wells. The test compounds (0.09 µl) were applied to the assay plate in 100% DMSO. The reaction was started by addition of 20 µl of [1,2$^3$H]-cortisone (0.1 µCi/100 mM) in assay buffer comprising 25 mM HEPES, 100 mM KCl, 5 mM NaCl, 2 mM $MgCl_2$ and 0.25 mM NADPH. The plate was agitated at 37° C. for 1 hour. At the same time, a stop solution comprising 20 mg/ml SPA-PVT beads, 1.6 mg/ml monoclonal cortisol antibody and 0.01 mM SSR110887 (inhibitor from the Biovitrium patent) in 50 mM HEPES, 1 M NaCl and 1 M KCl was stirred at room temperature. To stop the reaction, 25 µl of the stop solution were added to each well. The plate was agitated gently at room temperature for 1 further hour and then centrifuged at 500 $g_{av}$ for 1 min, in order that the SPA beads could settle out. The plate was then read in a Wallac-1450-Microbeta unit with a standard SPA program (counting time 1 min/well). The comparative compound was glycyrrhetinic acid.

Protein and radioactive substrate were dispensed with a Biomek FX unit (Beckman Coulter) for handling liquids. The test compounds were added with a Cybi-Well equipped with a 90 nl pin tool (CyBio).

Lit.: Solly 5, Mundt S S, Zokian H J, Juy-Fang Ding G, Hermanowski-Vosatka A, Strulovici B and Zheng W. High-throughput screening of 11β-Hydroxysteroid dehydrogenase type 1 in scintillation proximity format. Assay Drug Dev Technol 2005; 3:377-384.

TABLE 2

| Biological activity | |
| --- | --- |
| Example | IC50 (nM) |
| 1 | 31 |
| 2 | 575 |
| 3 | 24 |
| 4 | 63 |
| 5 | 8 |
| 6 | 4 |
| 9 | 5 |
| 10 | 104 |
| 12 | 3 |
| 13 | 5 |
| 14 | 236 |
| 17 | 27 |
| 18 | 4 |
| 19 | 11 |
| 20 | 13 |
| 25 | 25 |
| 26 | 742 |
| 27 | 62 |
| 28 | 445 |
| 29 | 15 |
| 30 | 11 |
| 31 | 34 |
| 32 | 4 |
| 33 | 9 |
| 34 | 353 |

It can be inferred from the test data that the compounds of the formula I inhibit 11 beta-HSD 1 (11beta-hydroxysteroid dehydrogenase type 1), and are thus of good suitability for treatment of hyperglycemia, insulin resistance, diabetes, obesity, lipid metabolism disorders, high blood pressure, cognitive improvement, elevated intraocular pressure, promotion of wound healing, and other diseases.

The preparation of some examples is described in detail hereinafter; the remaining compounds of the formula I were obtained analogously:

EXPERIMENTAL

Compounds 1-22 were synthesized by this preparation method:

(S)-3-(1,1-Dioxo-4-a,5,6,7,8,8a-hexahydro-1H-1lambda6-benzo[1,4,3]oxathiazin-3-ylamino)-3-phenylpropan-1-ol

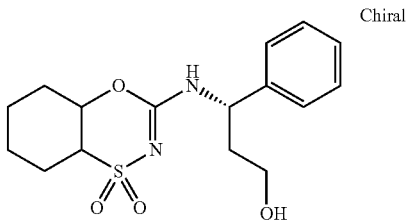 [SMILES: O=S1(=O)N=C(N[C@@H](CCO)c2ccccc2)OC2CCCCC21]

Under inert gas, 4 mmol of (S)-3-amino-3-phenylpropan-1-ol and 8 mmol of diisopropylethylamine were initially charged in 5 ml of dichloromethane and then, while cooling with ice, 5 mmol of 2-chlorocyclohexanesulfonyl isocyanate dissolved in 5 ml of dichloromethane were added dropwise and the mixture was stirred for 1 hour. The completeness of the conversion was checked by LCMS. If (S)-3-amino-3-phenylpropan-1-ol was still present, another 0.4 eq of 2-chlorocyclohexanesulfonyl isocyanate was added and the mixture was allowed to come to room temperature while stirring overnight. The reaction solution was diluted with 50 ml of dichloromethane and extracted twice with 20 ml of 10% $KHSO_4$ solution, and the organic phase was dried over $MgSO_4$ and concentrated by rotary evaporation. The residue was then admixed with 0.5 eq (based on the amine) of 0.1 N NaOH solution. Addition of dioxane (for example in the case of 20 ml of 0.1 M NaOH/5 ml of dioxane) and heated to 100° C. At 100° C., a clear solution is formed. If some starting material is still present, 1-2 drops of 1 N NaOH were added. After a further 30 minutes at 100° C., full conversion. After cooling, 30 ml of dichloromethane were added and the mixture was washed twice with 10 ml of saturated $Na_2CO_3$ solution. The aqueous solution was extracted once more with 20 ml of dichloromethane. The combined organic phases were dried over $MgSO_4$ and concentrated by rotary evaporation. The residue was dissolved in DMF and purified in a purification laboratory by means of preparative HPLC. This gave the product (170 mg) with a molecular weight of 338.4 g/mol ($C_{16}H_{22}N_2O_4S$); MS (ESI): m/e=339 (M+H+).

2-Chlorocyclohexanesulfonyl isocyanate

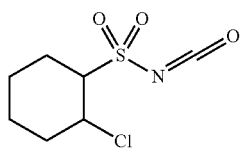 [SMILES: O=C=NS(=O)(=O)C1CCCCC1Cl]

Chemische Berichte 1970, 103(3), 663-669

The amines used are commercially available or can be prepared as follows:

(S)-4-Amino-4-phenylbutyric acid sodium salt

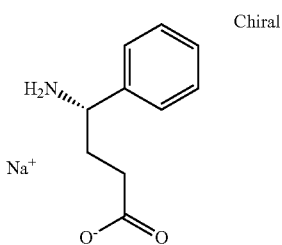 [SMILES: [Na+] ; N[C@@H](CCC(=O)[O-])c1ccccc1]

((S)-3-Cyano-1-phenylpropyl)carbamic acid tert-butyl ester (1.90 g) was suspended in 6 N HCl (50 ml) and stirred at 90° C. for 16 hours. The reaction solution was washed with dichloromethane (50 ml), basified with 12 N NaOH solution and concentrated. The residue contains the product (1.5 g) with a molecular weight of 179.2 g/mol ($C_{10}H_{13}NO_2$); MS (ESI): m/e=180 (M+H+).

(S)-4-Amino-4-phenylbutan-1-ol

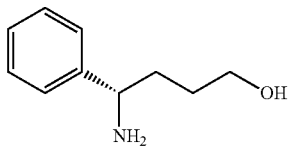 [SMILES: N[C@@H](CCCO)c1ccccc1]

(S)-4-Amino-4-phenylbutyric acid sodium salt (1.48 g) was added in portions to a suspension of lithium aluminum hydride (1.00 g) in THF (100 ml). The mixture was stirred at 50° C. for 4 hours and then admixed successively with water (1 ml), 6 N NaOH solution (3 ml) and again with water (3 ml), and filtered. The filtrate was concentrated and the residue was purified by column chromatography. This gave the product (70 mg) with a molecular weight of 165.2 g/mol ($C_{10}H_{15}NO$); MS (ESI): m/e=166 (M+H+).

(R)-4-Amino-4-phenylbutan-1-ol was prepared analogously:

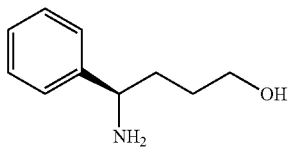 [SMILES: N[C@H](CCCO)c1ccccc1]

((S)-3-Cyano-1-phenylpropyl)carbamic acid tert-butyl ester

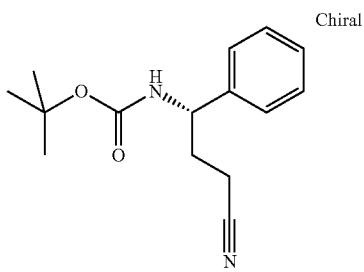 [SMILES: CC(C)(C)OC(=O)N[C@@H](CCC#N)c1ccccc1]

A solution of methanesulfonic acid (S)-3-tert-butoxycarbonylamino-3-phenylpropyl ester (2.0 g) and sodium cyanide (0.97 g) in DMF (10 ml) was stirred at 70° C. for 16 hours. The reaction mixture was partitioned between water (50 ml) and ethyl acetate (50 ml), and the aqueous phase was reextracted (2×50 ml). The combined organic phases were dried over magnesium sulfate and concentrated. This gave the product (1.7 g) with a molecular weight of 260.3 g/mol ($C_{15}H_{20}N_2O_2$); MS (ESI): m/e=261 (M+H+).

Methanesulfonic acid (S)-3-tert-butoxycarbonylamino-3-phenylpropyl ester

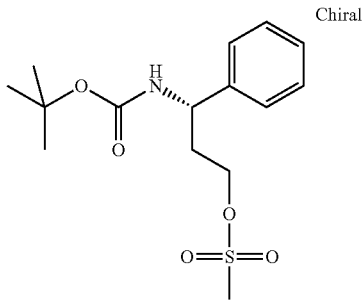 [SMILES: CC(C)(C)OC(=O)N[C@@H](CCOS(C)(=O)=O)c1ccccc1]

To a mixture of (S)-3-amino-3-phenylpropan-1-ol hydrochloride (1.50 g) and triethylamine (2.80 ml) in dichloromethane (100 ml) was added BOC anhydride (1.92 g), and the mixture was stirred at room temperature for 1 hour. The solution was washed with water and potassium carbonate solution and dried over magnesium sulfate. To the resulting solution were added pyridine (0.97 ml) and, dropwise at 0° C., methanesulfonyl chloride (0.68 ml). The solution was stirred at room temperature for 5 hours and then washed with 1 N HCl and water, dried over magnesium sulfate and concentrated. This gave the product (2.0 g) with a molecular weight of 329.4 g/mol ($C_{15}H_{23}NO_5S$); MS (ESI): m/e=330 (M+H+).

Carbamic acid (R)-2-amino-2-phenylethyl ester

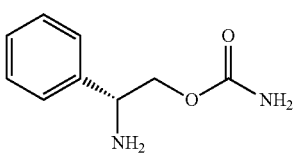 [SMILES: NC(=O)OC[C@H](N)c1ccccc1]

(R)-2-Amino-2-phenylethanol (0.60 g) was stirred with BOC anhydride (1.42 g) in dichloromethane (10 ml) at room temperature for 8 hours. The reaction solution was washed with sodium carbonate solution, dried over magnesium sulfate and concentrated. The residue was dissolved in dichloromethane (30 ml) and admixed at 0° C. with trichloroacetyl isocyanate (1.02 g). The mixture was stirred at room temperature for 2 hours and concentrated. The residue was taken up in methanol (15 ml), potassium carbonate solution (20 ml) was added and the mixture was stirred at room temperature for 5 hours. The precipitated product was filtered off with suction, washed repeatedly with water and dried. The product was dissolved in dichloromethane (10 ml), trifluoroacetic acid (5 ml) was added and the mixture was stirred at room temperature for 1.5 hours. The solvent was removed under reduced pressure and the residue was taken up in dichloromethane, washed with dilute sodium hydroxide solution, dried over magnesium sulfate and concentrated. This gave the product (533 mg) with a molecular weight of 180.2 g/mol ($C_9H_{12}N_2O_2$); MS (ESI): m/e=181 (M+H+).

Carbamic acid (S)-2-amino-2-phenylethyl ester was prepared analogously:

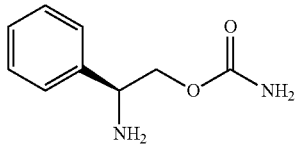 [SMILES: NC(=O)OC[C@@H](N)c1ccccc1]

1-[(S)-2-Amino-2-(4-fluorophenyl)ethyl]cyclopropanol

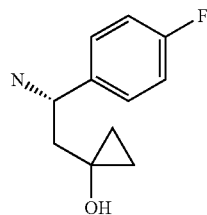 [SMILES: N[C@@H](CC1(O)CC1)c1ccc(F)cc1]

(S)-Methyl 3-amino-3-(4-fluorophenyl)propionate hydrochloride (4.5 g) was dissolved in THF (30 ml) and cooled to 0° C. After the addition of diisopropylethylamine (8.8 g), benzyl chloroformate (4.3 g) was slowly added dropwise and the mixture was stirred at 0° C. for 1 hour. The reaction mixture was concentrated by rotary evaporation, dichloromethane (50 ml) was added and the mixture was washed twice with NH$_4$Cl solution. Subsequently, the organic phase was dried with MgSO$_4$, filtered and concentrated. The residue (5.72 g) was taken up in THF, titanium tetraisopropoxide (0.49 g) was added, and ethylmagnesium bromide (3 N, 17.9 ml) was added dropwise over the course of 1 hour. After 24 hours, the reaction solution was poured into cold 2 N sulfuric acid (150 ml) and extracted three times with dichloromethane. The combined organic phases were dried with MgSO$_4$, filtered and concentrated. The residue was purified by preparative HPLC. The resulting (S)-1-(4-fluorophenyl)-2-(1-hydroxycyclopropyl)ethyl]carbamic acid benzyl ester (0.76 g) was dissolved in methanol (20 ml), 5% Pd/C was added and hydrogenation was effected under hydrogen pressure 2 bar. After filtration and concentration, the product (87 mg) was thus obtained with a molecular weight of 329.3 g/mol ($C_{19}H_{20}FNO_3$), MS (ESI): m/e=330 (M+H+).

((R)-2-Hydroxy-1-phenylethyl)carbamic acid tert-butyl ester

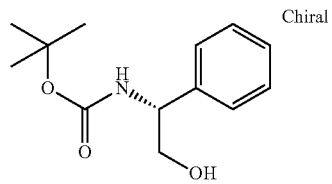 [SMILES: CC(C)(C)OC(=O)N[C@@H](CO)c1ccccc1]

(R)-2-Amino-2-phenylethanol (3 g) was dissolved in dichloromethane, and BOC anhydride (4.8 g) was added dropwise at room temperature. The mixture was then stirred at room temperature for 2.5 hours. The solvent was removed under reduced pressure. The substance was used further without further workup.

(S)-3-(tert-Butyldimethylsilanyloxy)-1-phenylpropylamine

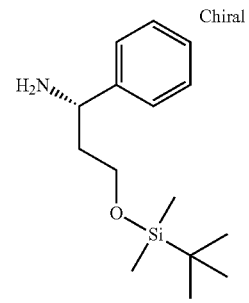 [SMILES: CC(C)(C)[Si](C)(C)OCC[C@H](N)c1ccccc1]

S-3-Amino-3-phenyl-1-propanol (4.72 g) was dissolved in dichloromethane (60 ml), triethylamine (6.36 g) and tert-butyldimethylchlorosilane (4.1 g) were added, and the mixture was stirred at room temperature for 3 hours. Then it was washed with water (3×50 ml) and dried using a phase separator cartridge. This gave the product (7 g) with a molecular weight of 265.5 g/mol ($C_{15}H_{27}NOSi$), MS (ESI): m/e=266 (M+H+).

Methylcarbamic acid (R)-2-phenylethyl ester

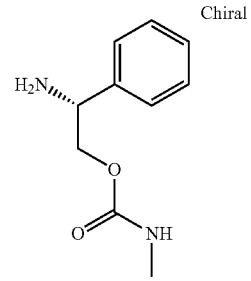

((R)-2-Hydroxy-1-phenylethyl)carbamic acid tert-butyl ester (1.2 g), carbonyldiimidazole (930 mg) and methylamine (2 N solution in THF, 3.8 ml) were dissolved in THF (10 ml) and stirred at room temperature for 16 hours. Then ethyl acetate (50 ml) was added and the organic solution was washed with potassium hydrogensulfate solution (2×20 ml), saturated sodium hydrogencarbonate solution (1×20 ml) and saturated sodium chloride solution (1×20 ml), dried using a silica gel cartridge and concentrated under reduced pressure.

The residue was then purified with ethyl acetate/n-heptane by normal phase chromatography. After the combination of the product fractions, the mixture was concentrated under reduced pressure, and the residue (550 mg) was admixed with dichloromethane (3 ml) and trifluoroacetic acid (1 ml), and stirred at room temperature for 1 hour. After addition of dichloromethane (20 ml), the mixture was washed with sodium hydrogencarbonate solution (2×20 ml) and saturated sodium chloride solution (1×20 ml), dried (sodium sulfate), filtered and concentrated under reduced pressure. This gave the product (259 mg) with a molecular weight of 194.3 g/mol ($C_{10}H_{14}N_2O_2$), MS (ESI): m/e=195 (M+H+).

The following compound was prepared in the same way:

Methylcarbamic acid (R)-2-amino-2-(4-fluorophenyl) ethyl ester

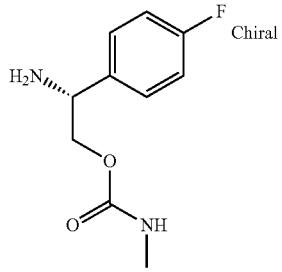

Compounds 23, 24, 29, 30 were synthesized by this preparation method:

(S)-3-((4aS,8aR)-1,1-Dioxo-4-a,5,6,7,8,8a-hexahydro-1H-1lambda6-benzo[1,4,3]oxathiazin-3-ylamino)-3-pyridin-3-ylpropionic acid ethyl ester

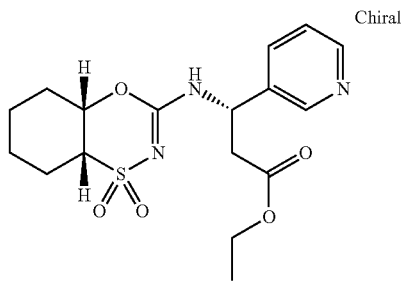 [SMILES: CCOC(=O)C[C@H](NC1=NS(=O)(=O)[C@@H]2CCCC[C@@H]2O1)c1cccnc1]

(S)-3-(4aS,8aR)-Amino-3-pyridin-3-ylpropionic acid ethyl ester dihydrochloride (1 g) in dry dichloromethane (10 ml) was admixed with triethylamine (2.05 m) and stirred at room temperature for 5 minutes. 1,1'-Thiocarbonyldiimidazole (717 mg) was added and then the mixture was stirred for a further 30 minutes. The solution was diluted with 1:1 diethyl ether/n-pentane (20 ml), washed with water (20 ml), dried with sodium sulfate, filtered and concentrated under reduced pressure. The residue was taken up in NMP (4 ml) (solution 1). cis-2-Hydroxycyclohexanesulfonamide (488 mg), dissolved in NMP (6 ml), was cooled to 0° C., sodium bis(trimethylsilyl)amide (2 N solution, 1.36 ml) was added and the mixture was stirred for 5 minutes. Solution 1 was then added at 0° C. and the mixture was stirred for a further 5 minutes. Subsequently, N-bromosuccinimide (485 mg) was added and the mixture was stirred for 3 minutes. Then it was diluted with water (100 ml) and extracted with ethyl acetate (3×30 ml). The combined organic phases were dried with sodium sulfate, filtered and concentrated under reduced pressure. Purification was effected by means of preparative HPLC. This gave the product (214 mg) with a molecular weight of 381.4 g/mol ($C_{17}H_{23}N_3O_5S$), MS (ESI): m/e=382 (M+H+).

(S)-3-((4aS,8aR)-1,1-Dioxo-4-a,5,6,7,8,8a-hexahydro-1H-1lambda6-benzo[1,4,3]oxathiazin-3-ylamino)-3-pyridin-3-ylpropan-1-ol

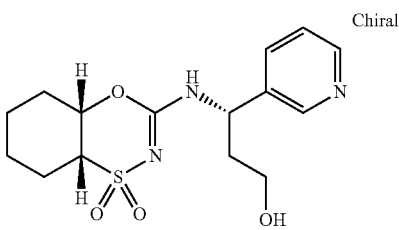 [SMILES: O=S1(=O)N=C(N[C@@H](CCO)c2cccnc2)O[C@H]2CCCC[C@H]21]

(S)-3-(1,1-Dioxo-4-a,5,6,7,8,8a-hexahydro-1H-1lambda6-benzo[1,4,3]oxathiazin-3-ylamino)-3-pyridin-3-ylpropionic acid ethyl ester (200 mg) was dissolved in dry dichloromethane (15 ml), diisobutylaluminum hydride (1 N solution, 2.65 ml) was added at −70° C. and the mixture was stirred for 1 hour. The mixture was admixed with acetone (0.25 ml) and acetic acid (0.3 ml) and brought to room temperature. The solvent was removed under reduced pressure and diluted with methanol (15 ml), and sodium borohydride (198 mg) was added in small portions at room temperature. After 1 hour, saturated aqueous Rochelle's salt solution was added and the mixture was stirred for 1 further hour. It was filtered and the filtrate was concentrated under reduced pressure. Purification was effected by means of preparative HPLC. This gave the product (23 mg) with a molecular weight of 339.4 g/mol ($C_{15}H_{21}N_3O_4S$), MS (ESI): m/e=340 (M+H+) as the hydrochloride salt.

Compounds 26-28 were synthesized by this preparation method:

(S)-3-(1,1-Dioxo-5,6,8,8a-tetrahydro-1H,4aH-4,7-dioxa-1lambda6-thia-2-azanaphthalen-3-ylamino)-3-phenylpropan-1-ol

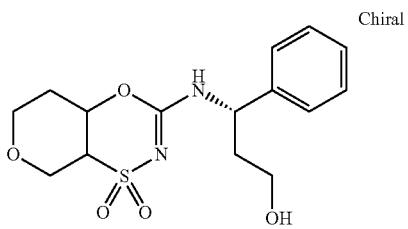 [SMILES: O=S1(=O)N=C(N[C@@H](CCO)c2ccccc2)OC2CCOCC21]

(S)-3-(tert-Butyldimethylsilanyloxy)-1-phenylpropylamine (273 mg) was dissolved in dry dichloromethane (2 ml). 1,1'-Thiocarbonyldiimidazole (216 mg) was added and then the mixture was stirred for a further 45 minutes. The solution was diluted with 1:1 diethyl ether/n-pentane (20 ml), washed with water (20 ml), dried with sodium sulfate, filtered and concentrated under reduced pressure. The residue was taken up in NMP (1 ml) (solution 1). 4-Hydroxytetrahydropyran-3-sulfonamide (200 mg), dissolved in NMP (2 ml), was cooled to 0° C., sodium bis(trimethylsilyl)amide (2 N solution, 0.55 ml) was added and the mixture was stirred for 5 minutes. Solution 1 was then added at 0° C. and the mixture was stirred for a further 10 minutes. Subsequently, N-bromosuccinimide (196 mg) was added and the mixture was stirred for 5 minutes. Then it was diluted with water (100 ml) and extracted with ethyl acetate (3×30 ml). The combined organic phases were dried with sodium sulfate, filtered and concentrated under reduced pressure. The residue was taken up in methanol (3 ml), concentrated HCl (0.3 ml) was added and the mixture was stirred at room temperature for 90 minutes. Then neutralization was effected with 1 N sodium hydroxide solution and the mixture was concentrated under reduced pressure. Purification was effected by means of preparative HPLC. This gave the cis/trans products (33 mg, 19 mg) with a molecular weight of 340.4 g/mol ($C_{15}H_{20}N_2O_5S$), MS (ESI): m/e=341 (M+H+).

Sulfamoyl Chloride

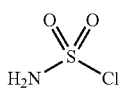

To a solution of chlorosulfonyl isocyanate (32.5 g) in methylene chloride (50 ml) was added formic acid in methylene chloride (50 ml) in portions over the course of 10 minutes. After 30 minutes at room temperature, methylene chloride (50 ml) was added once again. After 16 hours, a clear liquid with a pale yellowish glint had formed. Thereafter, the mixture was cooled to −18° C. in a freezer for 1 hour. The precipitate formed was filtered off with suction and dried in a vacuum drying cabinet. The dried precipitate (15.8 g) was stored under argon at −18° C.

2-Oxocyclohexanesulfonamide

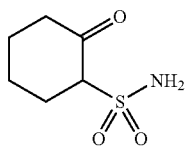 [SMILES: NS(=O)(=O)C1CCCCC1=O]

1-Piperidinocyclohexene (11.3 g) was dissolved in anhydrous THF (100 ml) under argon.

Thereafter, the mixture was cooled to −60° C. and sulfamoyl chloride (11.85 g) in anhydrous THF (100 ml) was added dropwise (temperature increase from −60° C. to about −40° C.). The mixture was then cooled to −60° C. Then a solution of Hünig's base (13.3 g) in anhydrous THF (50 ml) was added gradually. The mixture was warmed up to room temperature and stirred for 2 hours. An unstirrable oil was the result. The THF was decanted off, and the oily residue was dissolved in methanol and filtered through silica gel. Subsequently, the methanol was removed under reduced pressure. The residue was dissolved completely in boiling 1:1 ethyl acetate/n-heptane (40 ml). After cooling to room temperature, the solution was cooled to 5° C. in a refrigerator. The precipitate was subsequently filtered off with suction using a frit. This gave the product (5.3 g) with a molecular weight of 177.2 g/mol ($C_6H_{11}NO_3S$), MS (EST): m/e=178 (M+H+).

The following compounds were prepared in the same way:
4-Oxotetrahydropyran-3-sulfonamide

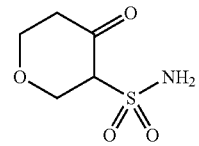 [SMILES: NS(=O)(=O)C1COCCC1=O]

5,5-Difluoro-2-oxocyclohexanesulfonamide

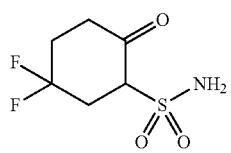 [SMILES: NS(=O)(=O)C1CC(F)(F)CCC1=O]

N-Sulfinyl-p-toluamide

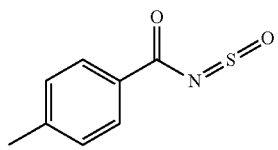

p-Toluamide (76 g) and pyridine (95.5 ml) were initially charged in dry ether (600 ml) and, while cooling with ice, thionyl chloride (70.2 g) in ether (200 ml) was added dropwise. The mixture was stirred at room temperature overnight. With exclusion of moisture, the pyridine hydrochloride was then filtered off and washed with ether (100 ml). The solution was concentrated under reduced pressure and the residue (83.5 g) was used without further purification.

3-p-Tolyl-4-a,5,6,7,8,8a-hexahydrobenzo[1,4,3]oxathiazine 1,1-dioxide

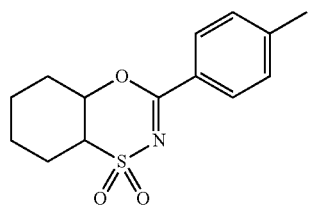 [SMILES: Cc1ccc(C2=NS(=O)(=O)C3CCCCC3O2)cc1]

N-Sulfinyl-p-toluamide (83.3 g) was dissolved in dichloromethane (300 ml), cyclohexene (81.1 g) was added and the mixture was stirred for 24 hours. The reaction solution was concentrated by rotary evaporation and taken up in ether (100 ml), and the product was isolated using a silica gel column (350 g) as follows. 1.5 l of 1:1 dichloromethane/ether; 500 ml of 3:2 dichloromethane/ether; 500 ml of 4:1 dichloromethane/ether; fractions each of 200 ml. The product-containing fractions were combined and concentrated by rotary evaporation, and the residue was stirred with 150 ml of ether/ 100 ml of n-pentane. Precipitated product was filtered off, washed with n-pentane (50 ml) and dried. This was followed by concentration under reduced pressure. The residue (24.6 g) was taken up in dichloromethane (200 ml) and 3-chloroperoxybenzoic acid was added in portions, in such a way that the temperature did not exceed 30° C. After addition had ended (45 minutes), the mixture was stirred overnight. The precipitated 3-chlorobenzoic acid was filtered off with suction, washed with dichloromethane (2×500 ml), sodium hydroxide (0.5 N solution, 100 ml) and sodium chloride solution (semiconcentrated, 250 ml), dried over MgSO$_4$, filtered and concentrated by rotary evaporation under reduced pressure. The crystalline residue (11.9 g) was slurried with 1:1 ether/n-pentane (100 ml), filtered off with suction, washed with n-pentane (100 ml) and dried under high vacuum. The product was separated into its enantiomers:

Column: Chiralpak AS-H/75, 5 μm, 250×4.6 mm
Eluent: heptane:isopropanol:methanol 3:2:1 (30° C., flow rate 1 ml/min)
Retention times: 7.728 minutes and 9.257 minutes.

4-Hydroxytetrahydropyran-3-sulfonamide

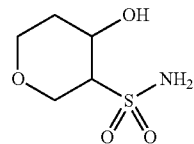

4-Oxotetrahydropyran-3-sulfonamide (1.09 g) was dissolved in 2:1 THF/methanol (110 ml), sodium borohydride (0.23 g) was added in portions and the mixture was stirred at room temperature for 18 hours. Concentrated hydrochloric acid was then used to set the pH to 2 and then the solvent was removed under reduced pressure. The residue was purified by chromatography (solvent: dichloromethane/methanol). This gave the product (0.65 g) with a molecular weight of 181.2 g/mol ($C_5H_{11}NO4S$).

The following compound was prepared in the same way:

5,5-Difluoro-2-hydroxy-cyclohexanesulfonamide

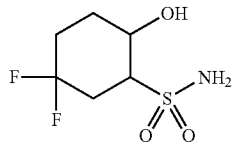 [SMILES: NS(=O)(=O)C1CC(F)(F)CCC1O]

2-Hydroxycyclohexanesulfonamide

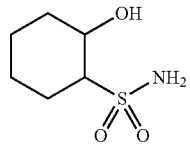 [SMILES: NS(=O)(=O)C1CCCCC1O]

3-p-Tolyl-4-a,5,6,7,8,8a-hexahydrobenzo[1,4,3]oxathiazine 1,1-dioxide (9.94 g) was heated in semiconcentrated aqueous sodium hydroxide solution (50 ml) and ethanol (10 ml) as a solubilizer to 100° C. for 18 hours. Then the ethanol was removed on a rotary evaporator, the aqueous solution was adjusted to pH 3.8 with concentrated HCl and cooled to room temperature, the precipitated tolyl acid was filtered off with suction and washed with a little water (10 ml), and the aqueous solution was washed with dichloromethane (100 ml). Subsequently, n-butanol (5×50 m) was used to extract the product from the aqueous phase, the solvent was removed on a rotary evaporator, and the residue was dissolved in ethanol (100 ml) and admixed with dichloromethane (100 ml). A small amount of undissolved solids were filtered off and the solution was concentrated by rotary evaporation. Subsequently, the residue was dissolved in water (100 ml) and freeze-dried. This gave the product (3.24 g) with a molecular weight of 179.2 g/mol ($C_6H_{13}NO_3S$), MS (EST): m/e=180 (M+H+).

2-Amino-2-phenylethanesulfonamide

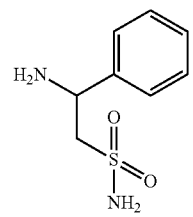

To a hot solution of hydroxylamine hydrochloride (27 mg) in water (0.02 ml) was added sodium ethoxide (130 mg) dissolved in ethanol (0.5 ml), and then the solution was cooled to 5° C. The suspension was filtered and the filtrate was admixed with 2-phenyleth-1-ene-1-sulfonamide (35 mg). Then the mixture was stirred at 100° C. for 7 hours and concentrated under reduced pressure. This gave the product with a molecular weight of 216.3 g/mol ($C_8H_{12}N_2O_3S$), MS (ESI): m/e=217 (M+H+).

The substance (1.81 g from a larger batch), without further workup, was dissolved in 2:1 1 N HCl/AcOH, zinc was added thereto and the mixture was stirred at room temperature. At first 10 equivalents of zinc were added, after 16 hours a further 18 equivalents of zinc were added, and the mixture was stirred for a further 2 hours. The reaction solution was adjusted to pH 9 with concentrated sodium hydroxide solution, and the precipitate formed was filtered through Celite and then washed with methanol (3×5 ml). To purify the substance, it was stirred with BOC anhydride (1.2 equivalents) for 2 days and then the methanol was removed under reduced pressure. After addition of water (30 ml), the mixture was extracted with ethyl acetate (2×30 ml), dried over MgSO$_4$ and concentrated by rotary evaporation under reduced pressure. The residue was purified via normal phase (20 g silica gel column; product elutes at ethyl acetate content about 50%). The fractions of value were combined and concentrated by rotary evaporation. The residue was taken up in dioxane (20 ml), hydrochloric acid (4 N, 10 ml) was added and the mixture was stirred at room temperature for 2 hours. Subsequently, the mixture was concentrated under reduced pressure, methanol was added and the mixture was concentrated again twice more, in order to remove water residues, and then the concentrate was dried under high vacuum. This gave the product (312 mg) with a molecular weight of 200.3 g/mol ($C_8H_{12}N_2O_2S$), MS (ESI): m/e=201 (M+H+) as the hydrochloride salt.

N-tert-Butylmethanesulfonamide

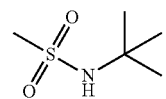

To a solution of methanesulfonyl chloride (7.7 ml) in dichloromethane (100 ml) was added dropwise tert-butylamine (23.1 ml) at 0° C., and the mixture was stirred for 5 minutes. Subsequently, the mixture was filtered and the filtrate was washed with 1 N hydrochloric acid (100 ml), dried with magnesium sulfate, filtered and concentrated under reduced pressure. This gave the product (14.7 g) with a molecular weight of 151.3 g/mol ($C_5H_{13}NO_2S$).

N-(tert-Butyl)-2-(4-fluorophenyl)-2-oxoethanesulfonamide

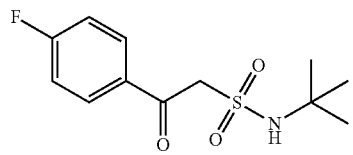 [SMILES: CC(C)(C)NS(=O)(=O)CC(=O)c1ccc(F)cc1]

N-tert-Butylmethanesulfonamide (1.00 g) was initially charged in THF (10 ml) and cooled to −78° C. n-Butyllithium (1.6 N in hexane, 9.00 ml) was added dropwise. Subsequently, the mixture was warmed up to 0° C. within 5 minutes, stirred for 5 further minutes and cooled again to −78° C. Methyl 4-fluorobenzoate (1.56 g) in THF (10 ml) dissolved and to −78° C. cooled. The solution prepared above was added dropwise at low temperature. After the addition had ended, the mixture was allowed to come to room temperature and stirred for a further 1 hour. After the addition of acetic acid (0.82 ml) and ethyl acetate (50 ml), the mixture was washed with saturated sodium hydrogencarbonate solution (50 ml) and saturated sodium chloride solution (50 ml). The organic phase was dried over magnesium sulfate, filtered and concentrated by rotary evaporation. Purification was effected via normal phase with an n-heptane/ethyl acetate gradient. The fractions of value were combined, concentrated by rotary evaporation and dried under reduced pressure. This gave the product (661 mg) with a molecular weight of 273.3 g/mol ($C_{12}H_{16}FNO_3S$), MS (EST): m/e=296 (M+Na⁺).

N-(tert-Butyl)-2-amino-2-(4-fluorophenyl)ethanesulfonamide

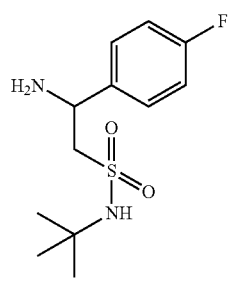 [SMILES: CC(C)(C)NS(=O)(=O)CC(N)c1ccc(F)cc1]

A solution of N-(tert-butyl)-2-(4-fluorophenyl)-2-oxoethanesulfonamide (657 mg), ammonium acetate (1.85 g) and sodium cyanoborohydride (166 mg) was stirred in methanol (12 ml) at 60° C. for 17 hours. The reaction solution was concentrated by rotary evaporation and the residue was taken up in ethyl acetate (50 ml). Then it was washed with 0.5 N aqueous sodium hydroxide solution (50 ml) and with saturated sodium chloride solution (50 ml), and the organic phase was dried over $MgSO_4$, filtered and concentrated under reduced pressure. This gave the product (697 mg) with a molecular weight of 274.3 g/mol ($C_{12}H_{19}FN_2O_2S$), MS (ESI): m/e=275 (M+H+).

2-((4aS,8aR)-1,1-Dioxo-4-a,5,6,7,8,8a-hexahydro-1H-1lambda6-benzo[1,4,3]oxathiazin-3-ylamino)-2-(4-fluorophenyl)ethanesulfonamide

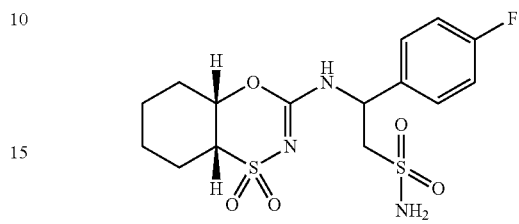

N-[tert-Butyl]-2-((4aS,8aR)-1,1-dioxo-4-a,5,6,7,8,8a-hexahydro-1H-1lambda6-benzo[1,4,3]oxathiazin-3-ylamino)-2-(4-fluorophenyl)ethanesulfonamide (50 mg) was admixed with trifluoroacetic acid (1 ml) and the mixture was stirred at room temperature for 5 hours. The solution was then purified by preparative HPLC. This gave the product (697 mg) with a molecular weight of 405.4 g/mol ($C_{15}H_{20}FN_3O_5S_2$), MS (ESI): m/e=406 (M+H+). 4a,8a-Dimethyl-3-(4-nitrophenoxy)-4-a,5,6,7,8,8a-hexahydrobenzo[1,4,3]oxathiazine 1,1-dioxide

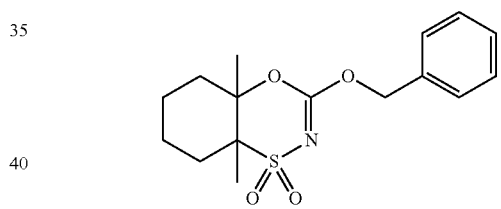

To a solution of chlorosulfonyl isocyanate (6 g) in dichloromethane (75 ml) was added benzyl alcohol (4.58 g), and the solution was stirred at room temperature for 1 hour. Subsequently, the solvent was removed under reduced pressure. The residue was taken up in THF (50 ml) and admixed with sodium hydride (95%, 1.77 g) at −78° C. The cooling was removed and the mixture was warmed up gradually to room temperature. Then 1,2-dimethylcyclohexene (4.17 g) was added and the mixture was heated to 35° C. After 3 hours, the mixture was poured onto ice (100 g) and then extracted with ethyl acetate (2×100 ml). The organic phase was dried with sodium sulfate, filtered and concentrated under reduced pressure. The residue (8 g) was purified by preparative HPLC. This gave the product (2.65 g) with a molecular weight of 323.4 g/mol (C15H21NO4S). The separation into the pure enantiomers was effected by chiral HPLC:

Column: Chiralpak AD-H/39, 5 μm, 250×4.6 mm

Eluent: heptane:ethanol 6:1 (30° C., flow rate 1 ml/min)

Retention times: 8.383 minutes (enantiomer 1) and 12.467 minutes (enantiomer 2).

Compounds 31-34 were synthesized by this preparation method:

(S)-3-(4a,8a-Dimethyl-1,1-dioxo-4-a,5,6,7,8,8a-hexahydro-1H-1lambda6-benzo[1,4,3]oxathiazin-3-ylamino)-3-phenylpropan-1-ol

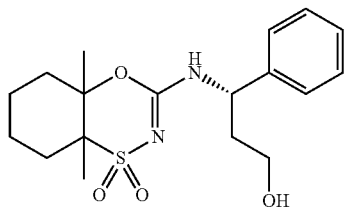 [SMILES: CC12CCCCC1(C)S(=O)(=O)N=C(N[C@@H](CCO)c1ccccc1)O2]

To a solution of enantiomerically pure 4a,8a-dimethyl-3-(4-nitrophenoxy)-4-a,5,6,7,8,8a-hexahydrobenzo[1,4,3]oxathiazine 1,1-dioxide enantiomer 1 (50 mg) in dichloromethane (2 ml) were added S-3-amino-3-phenylpropan-1-ol hydrochloride (30 mg) and diisopropylethylamine (50 mg). The solvent was removed under reduced pressure and the residue was left to stand for 16 hours. This was followed by purification by preparative HPLC. This gave the product (32 mg) with a molecular weight of 366.4 g/mol ($C_{18}H_{26}N_2O_4S$), MS (ESI): m/e=367 (M+H+).

(S)-3-(4a,8a-Dimethyl-1,1-dioxo-4-a,5,6,7,8,8a-hexahydro-1H-1lambda6-benzo[1,4,3]oxathiazin-3-ylamino)-3-pyridin-3-ylpropan-1-ol

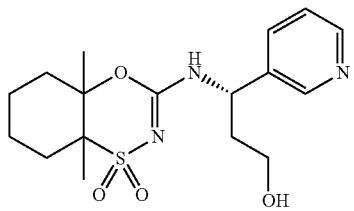 [SMILES: CC12CCCCC1(C)S(=O)(=O)N=C(N[C@@H](CCO)c1cccnc1)O2]

The invention claimed is:

1. A compound of the formula I

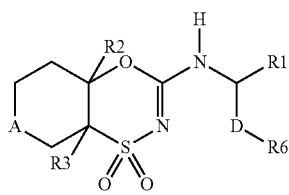

in which

A is $CH_2$, $CF_2$, O;

D is ($C_1$-$C_6$)-alkylene, ($C_3$-$C_8$)-cycloalkylene, ($C_1$-$C_6$)-alkylene-($C_3$-$C_8$)-cycloalkylene;

R1 is —$(CH_2)_n$-aryl, where the aryl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl$)_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—($C_1$-$C_6$)-alkyl, $CONH_2$, $CONH(C_1$-$C_6)$-alkyl, $CON((C_1$-$C_6)$-alkyl$)_2$, $SF_5$;

—$(CH_2)_n$-heteroaryl, where the heteroaryl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl$)_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—($C_1$-$C_6$)-alkyl, $CONH_2$, $CONH(C_1$-$C_6)$-alkyl, C ON(($C_1$-$C_6)$-alkyl$)_2$, $SF_5$;

n is 0, 1, 2;

R2, R3 are each independently H, ($C_1$-$C_6$)-alkyl;

R6 is OH or $SO_2NH_2$;

and pharmaceutically acceptable salts thereof.

2. The compound of claim 1, wherein

A is $CH_2$;

D is ($C_1$-$C_6$)-alkylene, ($C_3$-$C_8$)-cycloalkylene;

R1 is —$(CH_2)_n$-phenyl, —$(CH_2)_n$-pyridinyl, where the phenyl radical or pyridinyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl$)_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—($C_1$-$C_6$)-alkyl, $CONH_2$, $CONH(C_1$-$C_6)$-alkyl, $CON((C_1$-$C_6)$-alkyl$)_2$, $SF_5$;

n is 0, 1, 2;

R2, R3 are each independently H, ($C_1$-$C_6$)-alkyl;

R6 is OH or $SO_2NH_2$;

and pharmaceutically acceptable salts thereof.

3. The compound of claim 1, wherein

A is $CH_2$;

D is ($C_1$-$C_6$)-alkylene;

R1 is phenyl, pyridine where the phenyl radical or pyridinyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl$)_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—($C_1$-$C_6$)-alkyl, $CONH_2$, $CONH(C_1$-$C_6)$-alkyl, $CON((C_1$-$C_6)$-alkyl$)_2$, $SF_5$;

R2, R3 are each independently H, ($C_1$-$C_6$)-alkyl;

R6 is OH;

and pharmaceutically acceptable salts thereof.

4. The compound of claim 1, wherein

A is $CH_2$;

D is ($C_1$-$C_2$)-alkylene;

R1 is phenyl, where the phenyl radical may be mono- to trisubstituted by F, Cl, Br, I, OH, $CF_3$, $CHF_2$, $CH_2F$, $NO_2$, CN, $OCF_3$, $OCHF_2$, O—($C_1$-$C_6$)-alkyl, ($C_1$-$C_6$)-alkyl, $NH_2$, $NH(C_1$-$C_6)$-alkyl, $N((C_1$-$C_6)$-alkyl$)_2$, $SO_2$—$CH_3$, $SO_2$—$NH_2$, $SO_2$—$NH(C_1$-$C_6)$-alkyl, $SO_2$—$N((C_1$-$C_6)$-alkyl$)_2$, COOH, COO—($C_1$-$C_6$)-alkyl, $CONH_2$, $CONH(C_1$-$C_6)$-alkyl, $CON((C_1$-$C_6)$-alkyl$)_2$, $SF_5$;

R2, R3 are each independently H, ($C_1$-$C_6$)-alkyl;

R6 is OH;

and pharmaceutically acceptable salts thereof.

5. A pharmaceutical composition comprising the compound of claim 1, or a pharmaceutically acceptable salt thereof, and a pharmaceutically acceptable carrier and/or excipient.

6. The pharmaceutical composition of claim 5, further comprising at least one further active ingredient.

7. The pharmaceutical composition of claim 6, wherein said active ingredient is one or more antidiabetics, active hypoglycemic ingredients, HMG-CoA reductase inhibitors, cholesterol absorption inhibitors, PPAR gamma agonists, PPAR alpha agonists, PPAR alpha/gamma agonists, PPAR delta agonists, fibrates, MTP inhibitors, bile acid absorption inhibitors, CETP inhibitors, polymeric bile acid adsorbers, LDL receptor inducers, ACAT inhibitors, antioxidants, lipoprotein lipase inhibitors, ATP citrate lyase inhibitors, squalene synthetase inhibitors, lipoprotein(a) antagonists, HM74A receptor agonists, lipase inhibitors, insulins, sulfonylureas, biguanides, meglitinides, thiazolidinediones, α-glucosidase inhibitors, active ingredients which act on the ATP-dependent potassium channel of the beta cells, glycogen phosphorylase inhibitors, glucagon receptor antagonists, activators of glucokinase, inhibitors of gluconeogenesis, inhibitors of fructose 1,6-biphosphatase, modulators of glucose transporter 4, inhibitors of glutamine:fructose-6-phosphate amidotransferase, inhibitors of dipeptidylpeptidase IV, inhibitors of 11-beta-hydroxysteroid dehydrogenase 1, inhibitors of protein tyrosine phosphatase 1B, modulators of the sodium-dependent glucose transporter 1 or 2, GPR40 modulators, inhibitors of hormone-sensitive lipase, inhibitors of acetyl-CoA carboxylase, inhibitors of phosphoenolpyruvate carboxykinase, inhibitors of glycogen synthase kinase-3 beta, inhibitors of protein kinase C beta, endothelin-A receptor antagonists, inhibitors of I kappaB kinase, modulators of the glucocorticoid receptor, CART agonists, NPY agonists, MC4 agonists, orexin agonists, H3 agonists, TNF agonists, CRF agonists, CRF BP antagonists, urocortin agonists, β3 agonists, CB1 receptor antagonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, decoupling protein 2 or 3 modulators, leptin agonists, DA agonists, lipase/amylase inhibitors, PPAR modulators, RXR modulators or TR β agonists or amphetamines.

8. A process for preparing a pharmaceutical composition comprising mixing the compound of claim 1 with a pharmaceutically suitable carrier and converting said mixture to a form suitable for administration.

9. A method of treating hyperglycemia comprising administering to a patient in need thereof a therapeutically effective amount of the pharmaceutical composition of claim 5.

10. A method of treating diabetes comprising administering to a patient in need thereof a therapeutically effective amount of the pharmaceutical composition of claim 5.

11. A method of treating insulin resistance comprising administering to a patient in need thereof a therapeutically effective amount of the pharmaceutical composition of claim 5.

12. A kit comprising separate packages of
   a) an effective amount of the compound of claim 1 and
   b) an effective amount of a further active medicament ingredient.

* * * * *